US012590155B2

(12) United States Patent
Zhou et al.

(10) Patent No.: US 12,590,155 B2
(45) Date of Patent: Mar. 31, 2026

(54) MOLECULES BINDING PD-L1 AND USES THEREOF

(71) Applicant: Beijing Mabworks Biotech Co., Ltd, Beijing (CN)

(72) Inventors: Xuechen Zhou, Beijing (CN); Guangzhong Lin, Beijing (CN); Jiangmei Li, Beijing (CN); Wenqi Hu, Beijing (CN); Feng Li, Beijing (CN)

(73) Assignee: BEIJING MABWORKS BIOTECH CO., LTD., Beijing (CN)

( * ) Notice: Subject to any disclaimer, the term of this patent is extended or adjusted under 35 U.S.C. 154(b) by 502 days.

(21) Appl. No.: 18/323,645

(22) Filed: May 25, 2023

(65) Prior Publication Data

US 2023/0382995 A1     Nov. 30, 2023

(30) Foreign Application Priority Data

May 31, 2022     (CN) ......................... 202210611228.9

(51) Int. Cl.
| | |
|---|---|
| *A61P 35/00* | (2006.01) |
| *C07K 16/28* | (2006.01) |
| *A61K 39/00* | (2006.01) |

(52) U.S. Cl.
CPC .......... *C07K 16/2827* (2013.01); *A61P 35/00* (2018.01); *A61K 2039/505* (2013.01); *C07K 2317/24* (2013.01); *C07K 2317/33* (2013.01); *C07K 2317/569* (2013.01); *C07K 2317/64* (2013.01); *C07K 2317/76* (2013.01); *C07K 2317/92* (2013.01)

(58) Field of Classification Search
CPC ............ C07K 16/2827; C07K 2317/24; C07K 2317/33; C07K 2317/569; C07K 2317/64; C07K 2317/76; C07K 2317/92; A61P 35/00; A61K 2039/505
See application file for complete search history.

(56) References Cited

U.S. PATENT DOCUMENTS 10,183,995 B2 *   1/2019   Blanchetot ........... A61K 39/395

* cited by examiner

*Primary Examiner* — Joanne Hama
*Assistant Examiner* — Hannah Sunshine
(74) *Attorney, Agent, or Firm* — Duane Morris LLP; Thomas J. Kowalski

(57) ABSTRACT

Disclosed is a molecule, e.g., a single-domain antibody, or a heavy chain only antibody, that specifically binds human PD-L1, and its use in treating diseases such as tumors.

17 Claims, 8 Drawing Sheets

Specification includes a Sequence Listing.

A

B

A

B

A

B

A

- ◆ 10CA192-Fc
- ● 10CA192-V$_H$H1-Fc
- ▲ 10CA192-V$_H$H2-Fc
- ▼ 10CA192-V$_H$H3-Fc
- ◆ 10CA192-V$_H$H4-Fc
- ● 10CA192-V$_H$H5-Fc

B

- ◆ 10CA192-Fc
- ● 10CA192-V$_H$H1-Fc
- ▲ 10CA192-V$_H$H2-Fc
- ▼ 10CA192-V$_H$H3-Fc
- ◆ 10CA192-V$_H$H4-Fc
- ● 10CA192-V$_H$H5-Fc

SEQUENCE LISTING

Sequence total quantity: 13
SEQ ID NO: 1              moltype = AA  length = 5
FEATURE                   Location/Qualifiers
source                    1..5
                          mol_type = protein
                          organism = synthetic construct
SEQUENCE: 1
DYAMT                                                                              5

SEQ ID NO: 2              moltype = AA  length = 17
FEATURE                   Location/Qualifiers
source                    1..17
                          mol_type = protein
                          organism = synthetic construct
VARIANT                   12
                          note = T or L
VARIANT                   13
                          note = N or D
VARIANT                   15
                          note = A or V
SEQUENCE: 2
TINSGGQSSS YXBSXKG                                                                 17

SEQ ID NO: 3              moltype = AA  length = 9
FEATURE                   Location/Qualifiers
source                    1..9
                          mol_type = protein
                          organism = synthetic construct
VARIANT                   8
                          note = K or A -continued

```
SEQUENCE: 3
GVYMPWKXP                                                                    9

SEQ ID NO: 4              moltype = AA  length = 118
FEATURE                   Location/Qualifiers
source                    1..118
                          mol_type = protein
                          organism = synthetic construct
SEQUENCE: 4
QVQLQESGGG LVQPGGSLRL SCVASGFAFS DYAMTWVRQA PGKGLEWVST INSGGQSSSY   60
TNSAKGRFTT SRDNAKNTLY LQLNSLKIED TAMYYCSQGV YMPWKKPKGQ GTQVTVSS     118

SEQ ID NO: 5              moltype = AA  length = 118
FEATURE                   Location/Qualifiers
source                    1..118
                          mol_type = protein
                          organism = synthetic construct
SEQUENCE: 5
QVQLLESGGG LVQPGGSLRL SCAASGFAFS DYAMTWVRQA PGKGLEWVST INSGGQSSSY   60
TNSAKGRFTT SRDNSKNTLY LQMNSLRAED TAVYYCAKGV YMPWKKPKGQ GTLVTVSS     118

SEQ ID NO: 6              moltype = AA  length = 118
FEATURE                   Location/Qualifiers
source                    1..118
                          mol_type = protein
                          organism = synthetic construct
SEQUENCE: 6
QVQLLESGGG LVQPGGSLRL SCAASGFAVS DYAMTWVRQA PGKGLEWVST INSGGQSSSY   60
TNSAKGRFTI SRDNSKNTLY LQMNSLRAED TAVYYCSQGV YMPWKKPKGQ GTLVTVSS     118

SEQ ID NO: 7              moltype = AA  length = 118
FEATURE                   Location/Qualifiers
source                    1..118
                          mol_type = protein
                          organism = synthetic construct
SEQUENCE: 7
QVQLQESGGG SVQAGGSLML SCAASGFAFS DYAMTWVRQA PGKGLEWVST INSGGQSSSY   60
LDSVKGRFTS TRDNAKNMLY LQLNSLKIED TAMYYCSQGV YMPWKAPKGQ GTQVTVSS     118

SEQ ID NO: 8              moltype = AA  length = 118
FEATURE                   Location/Qualifiers
source                    1..118
                          mol_type = protein
                          organism = synthetic construct
SEQUENCE: 8
QVQLLESGGG LVQPGGSLRL SCAASGFAFS DYAMTWVRQA PGKGLEWVST INSGGQSSSY   60
LDSVKGRFTI SRDNSKNTLY LQMNSLRAED TAVYYCAKGV YMPWKAPWGQ GTLVTVSS     118

SEQ ID NO: 9              moltype = AA  length = 118
FEATURE                   Location/Qualifiers
source                    1..118
                          mol_type = protein
                          organism = synthetic construct
SEQUENCE: 9
QVQLLESGGG LVQPGGSLRL SCAASGFAFS DYAMTWVRQA PGKGLEWVST INSGGQSSSY   60
LDSVKGRFTS SRDNSKNTLY LQMNSLRAED TAVYYCAKGV YMPWKAPKGQ GTLVTVSS     118

SEQ ID NO: 10             moltype = AA  length = 232
FEATURE                   Location/Qualifiers
source                    1..232
                          mol_type = protein
                          organism = synthetic construct
SEQUENCE: 10
EPKSCDKTHT CPPCPAPELL GGPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPAPIEKT   120
ISKAKGQPRE PQVYTLPPSR EEMTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 11             moltype = AA  length = 290
FEATURE                   Location/Qualifiers
source                    1..290
                          mol_type = protein
                          organism = synthetic construct
SEQUENCE: 11
MRIFAVFIFM TYWHLLNAFT VTVPKDLYVV EYGSNMTIEC KFPVEKQLDL AALIVYWEME   60
DKNIIQFVHG EEDLKVQHSS YRQRARLLKD QLSLGNAALQ ITDVKLQDAG VYRCMISYGG   120
ADYKRITVKV NAPYNKINQR ILVVDPVTSE HELTCQAEGY PKAEVIWTSS DHQVLSGKTT   180
TTNSKREEKL FNVTSTLRIN TTTNEIFYCT FRRLDPEENH TAELVIPELP LAHPPNERTH   240
LVILGAILLC LGVALTFIFR LRKGRMMDVK KCGIQDTNSK KQSDTHLEET             290
```

-continued

```
SEQ ID NO: 12          moltype = AA  length = 290
FEATURE                Location/Qualifiers
source                 1..290
                       mol_type = protein
                       organism = synthetic construct
SEQUENCE: 12
MRIFAVFIFT IYWHLLNAFT VTVPKDLYVV EYGSNMTIEC KFPVEKQLDL TSLIVYWEME  60
DKNIIQFVHG EEDLKVQHSN YRQRAQLLKD QLSLGNAALR ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL LNVTSTLRIN TTANEIFYCI FRRLDPEENH TAELVIPELP LALPPNERTH  240
LVILGAIFLL LGVALTFIFY LRKGRMMDMK KCGIRVTNSK KQRDTQLEET             290

SEQ ID NO: 13          moltype = AA  length = 290
FEATURE                Location/Qualifiers
source                 1..290
                       mol_type = protein
                       organism = synthetic construct
SEQUENCE: 13
MRIFAGIIFT ACCHLLRAFT ITAPKDLYVV EYGSNVTMEC RFPVERELDL LALVVYWEKE  60
DEQVIQFVAG EEDLKPQHSN FRGRASLPKD QLLKGNAALQ ITDVKLQDAG VYCCIISYGG  120
ADYKRITLKV NAPYRKINQR ISVDPATSEH ELICQAEGYP EAEVIWTNSD HQPVSGKRSV  180
TTSRTEGMLL NVTSSLRVNA TANDVFYCTF WRSQPGQNHT AELIIPELPA THPPQNRTHW  240
VLLGSILLFL IVVSTVLLFL RKQVRMLDVE KCGVEDTSSK NRNDTQFEET             290
```

MOLECULES BINDING PD-L1 AND USES THEREOF

INCORPORATION BY REFERENCE

This application claims priority to Chinese Patent Application No. 202210611228.9 filed on May 31, 2022.

The foregoing application, and all documents cited therein or during its prosecution ("appln cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

SEQUENCE STATEMENT

The instant application contains a Sequence Listing XML labeled "55556-00102SequenceListingXML" which was created on May 24, 2023 and is 15.1 bytes. The entire content of the sequence listing is incorporated herein by reference in its entirety.

FIELD OF THE INVENTION

The present disclosure relates to a molecule, e.g., a single-domain antibody, a heavy chain only antibody or an antigen binding fragment thereof, that specifically binds human PD-L1, and its uses in e.g., treatment of a disease associated with PD-L1, including tumors and infectious diseases.

BACKGROUND OF THE INVENTION

Cancer cells may survive and proliferate due to the immune tolerance as mediated by e.g., regulatory T cells (Tregs), immune-suppressive cytokines and chemokines, and/or inhibitory immune checkpoint molecules. The PD-1, PD-L1 and CTLA-4 are the most studied immune checkpoint molecules, several antibodies targeting these molecules have been marketed for cancer treatment, such as Yervoy® ipilimumab, Keytruda® pembrolizumab, and Opdivo® nivolumab.

CTLA-4 provides inhibitory signals at the initial stage of $CD4^+$ T cell activation and $CD4^+$ T cell-mediated help for $CD8^+$ T cells, while the PD-1 pathway mainly modulates the activated $CD8^+$ T cells at the later stage of an immune response. In particular, in the immune activation process, the naïve T cell recognizes an antigen displayed in the major histocompatibility complex (MHC) on the surface of an antigen-presenting cell (APC), and then binds its CD28 molecules to the B7 molecules on the APC, resulting in T cell proliferation, inflammatory cytokine release, and T cell migration. With the T cell activation, CTLA-4 expression increases to compete with the CD28 molecules over B7 binding, wherein CTLA-4's binding affinity to the B7 molecules is much higher than that of CD28. Hours or days post the initiation of T cell activation. PD-1 expression emerges on e.g., tumor infiltrating lymphocytes (TILs). While the $CD4^+$ Th1 cells and $CD8^+$ T cells in the tumor microenvironment (TME) produce interferon-γ (IFN-γ), which on one side triggers macrophage-mediated tumor cell death, and on the other side upregulates PD-L1 expression on the macrophages and tumor cells (including solid and hematological tumor cells). Upon the engagement of the PD-1 molecules on the tumor-specific $CD8^+$ T cells with the PD-L1 molecules in the TME, $CD8^+$ T cells will undergo anergy. The CTLA-4 molecules expressed on Tregs may further prevent $CD8^+$ T cells from secreting cytokines and killing tumors in the TME (Topalian S et al., (2016) *Nat Rev Cancer* 16(5): 275-287). In recent years, therapies targeting the PD-1/PD-L1 pathway, in view the potent clinical efficacy, durable responses and low toxicity, have attracted many scientists' attention, but not all patients are responsive to them (Gong J et al., (2018) *J Immunother Cancer* 6(1):8). Such therapies do not act on the tumors directly, but release the suppressive effect of the PD-1-PD-L1 signaling on the immune system.

In addition, the PD-1/PD-L1 pathway blockade also showed positive results in treating acute or chronic viral, bacterial and parasitic infections in pre-clinical and clinical researches (Jubel J M et al., (2020) *Front Immunol.* 11:487). For example, the administration of anti-PD-L1 antibodies increased IFN-γ, IL-2 and TNFα levels, enhanced T cell function, and alleviated viremia in chronic infection of e.g., hepatitis B virus (HBV), hepatitis C virus (HCV), human immunodeficiency virus (HIV), or simian immunodeficiency virus (SIV).

In 1993, Belgian scientists discovered a unique single-domain antibody (sdAb) in the serum of camels (Hamers-Casterman C et al., (1993) *Nature.* 363(6428): 446-448) which lacks the light chain and contains only one variable region ($V_HH$) in the heavy chain. It is the smallest antibody as ever till now with a size at about 15 kDa, and referred to as the nanobody (Nb) as well. Compared to the IgG antibodies, the sdAbs are highly soluble and stable, longer in CD3 size with a high antigen binding affinity and specificity, and highly homologous to human heavy chain variable regions. Further, the sdAbs can be well expressed at a high level (Muyldermans S., (2001) *Reviews in Molecular Biotechnology,* 74: 277-302). With these characteristics, the sdAb has become an attractive candidate for development of antibody-based therapeutics.

Citation or identification of any document in this application is not an admission that such document is available as prior art to the present invention.

SUMMARY OF THE INVENTION

The inventors of the application have designed and prepared some PD-L1-binding molecules, which, compared to the prior art antibodies such as atezolizumab, have i) comparable, if not higher, binding affinity/activity to PD-L1, ii) comparable, if not higher, blocking activity on PD-1-PD-L1 interaction, iii) comparable, if not higher, ability to active T cells, and/or (iv) comparable, if not higher, in vivo anti-tumor efficacy.

In one aspect, the disclosure provides an isolated single-domain antibody, that binds PD-L1 (e.g., human and monkey PD-L1s), which may comprise a variable region that may comprise a CDR1, a CDR2 and a CDR3, wherein the CDR1, the CDR2 and the CDR3 may respectively comprise amino acid sequences having at least 85%, 86%, 87%, 88%, 89%, 90%, 91%, 92%, 93%, 94%, 95%, 96%, 97%, 98%, 99% or 100% sequence identity to i) SEQ ID NOs: 1, 2 (X1=T, B=N, X2=A) and 3 (X=K); or ii) SEQ ID NOs: 1, 2 (X1=L, B=D, X2=V) and 3 (X=A). The variable region may comprise an amino acid sequence having at least 85%, 86%, 87%, 88%, 89%, 90%, 91%, 92%, 93%, 94%, 95%, 96%, 97%, 98%, 99% or 100% sequence identity to SEQ ID NOs: 4, 5, 6, 7, 8 or 9.

The single-domain antibody of the disclosure may be camelid or humanized.

The disclosure provides an isolated single-domain antibody, that specifically binds PD-L1, which may comprise a variable region comprising a CDR1, a CDR2 and a CDR3, wherein the CDR1, the CDR2 and the CDR3 may comprise the CDR1, CDR2 and CDR3 sequences from a single-domain antibody comprising the amino acid sequence of SEQ ID NOs: 4, 5, 6, 7, 8 or 9.

The single-domain antibody of the disclosure may be camelid or humanized.

In another aspect, the disclosure provides a molecule that specifically binds PD-L1, which may comprise a heavy chain variable region that may comprise a CDR1, a CDR2 and a CDR3, wherein the CDR1, the CDR2 and the CDR3 may respectively comprise amino acid sequences having at least 85%, 86%, 87%, 88%, 89%, 90%, 91%, 92%, 93%, 94%, 95%, 96%, 97%, 98%, 99% or 100% sequence identity to i) SEQ ID NOs: 1, 2 (X1=T, B=N, X2=A) and 3 (X=K); or ii) SEQ ID NOs: 1, 2 (X1=L, B=D, X2=V) and 3 (X=A). The heavy chain variable region in the molecule of the disclosure may comprise an amino acid sequence having at least 85%, 86%, 87%, 88%, 89%, 90%, 91%, 92%, 93%, 94%, 95%, 96%, 97%, 98%, 99% or 100% sequence identity to SEQ ID NOs: 4, 5, 6, 7, 8 or 9.

The molecule of the disclosure may be a single-domain antibody. The single-domain antibody of the disclosure may be camelid or humanized.

The molecule may be a recombinant protein comprising the heavy chain variable region and an immunoglobulin heavy chain constant region. The immunoglobulin heavy chain constant region may be a IgG, IgD, IgA, IgM or IgB heavy chain constant region, e.g., IgG1, IgG2, IgG3 or IgG4 heavy chain constant region, or a functional fragment thereof, e.g., a Fc region. In certain embodiments, the heavy chain constant region may comprise a hinge region, a $C_{H2}$ domain and a $C_{H3}$ domain. In certain embodiments, the heavy chain constant region may comprise a $C_{H2}$ domain and a $C_{H3}$ domain. In certain embodiments, the heavy chain constant region may be human IgG1 heavy chain constant region or a functional fragment thereof, comprising the amino acid sequence of e.g., SEQ ID NO: 10. The C-terminus of the heavy chain variable region may be linked to the N-terminus of the heavy chain constant region or the functional fragment thereof.

The molecule of the disclosure may be a dimer comprising two copies of the recombinant fusion proteins above (e.g., the recombinant fusion protein comprising the heavy chain variable region and an Fc region) linked via e.g., one or more disulfide bonds. In certain embodiments, the molecule of the disclosure may a homologous dimer of the recombinant fusion protein. In certain embodiments, the molecule of the disclosure may be a heterologous dimer of the recombinant fusion protein.

In certain embodiments, the molecule of the disclosure may be a heavy chain only antibody (HCAb) or an antigen binding fragment thereof. The heavy chain only antibody or the antigen binding fragment thereof may comprise the heavy chain variable region of the disclosure linked to an immunoglobulin heavy chain constant region described above. The heavy chain only antibody or the antigen binding fragment thereof may comprise two heavy chains, or consists of two heavy chains, wherein at least one of the heavy chain comprises the heavy chain variable region linked to an immunoglobulin heavy chain constant region described above. The heavy chain only antibody or the antigen binding fragment thereof may be camelid, chimeric or humanized.

The single-domain antibody and the molecule of the disclosure may a) bind PD-L1, b) inhibit PD-1-PD-L1 binding/interaction, c) activate T cells, and/or d) have in vivo anti-tumor activity.

The disclosure also provides an immunoconjugate that may comprise the single-domain antibody or the molecule of the disclosure, linked to a therapeutic agent such as a cytotoxin or an anti-cancer agent. The disclosure further provides a bispecific molecule that may comprise the single-domain antibody or the molecule of the disclosure, linked to a second functional moiety (e.g., a second antibody) having a different binding specificity than the single-domain antibody or the molecule of the disclosure. The single-domain antibody or the molecule of the disclosure may be made into part of a chimeric antigen receptor (CAR) or an engineered T cell receptor (TCR). Also provided is an immune cell that may comprise the CAR and/or the TCR, such as a T cell and a NK cell. The single-domain antibody or the molecule of the disclosure can also be encoded by or used in conjunction with an oncolytic virus.

The disclosure also provides a nucleic acid molecule encoding the single-domain antibody, the molecule (including the heavy chain only antibody or the antigen binding fragment thereof), the immunoconjugate, the bispecific molecule, the CAR or the TCR, as well as an expression vectors that may comprise the nucleic acid molecule and a host cell that may comprise the expression vector or have the nucleic acid molecule integrated into its genome.

A method for preparing the single-domain antibody, the molecule, the immunoconjugate, the bispecific molecule, the CAR or the TCR, using the host cell above is also provided, that may comprise steps of (i) expressing any of these molecules in the host cell and (ii) isolating the molecules from the host cell or its cell culture.

The disclosure further provides a composition, e.g., a pharmaceutical composition, which may comprise the single-domain antibody, the molecule (including the heavy chain only antibody or the antigen binding fragment thereof), the immunoconjugate, the bispecific molecule, the CAR or the TCR, the nucleic acid molecule, the expression vector or the host cell of the disclosure. In certain embodiments, the composition may be a pharmaceutical composition that may contain a pharmaceutically acceptable carrier.

In another aspect, the disclosure provides a method for treating or alleviating a PD-L1 associated disease in a subject in need thereof, comprising administering to the subject a therapeutically effective amount of the pharmaceutical composition of the disclosure.

The PD-L1 associated disease may be a tumor. The tumor may be a solid tumor or a hematological tumor, including, but not limited to, melanoma, lung cancer (e.g., non-small cell lung cancer), urothelial carcinoma, renal cell carcinoma, head and neck cancer, Hodgkin lymphoma, cancer with microsatellite instability or mismatch repair deficiency, gastric cancer, colorectal cancer, liver cancer (e.g., hepatocellular carcinoma), colon adenocarcinoma, and Merkel cell carcinoma. In certain embodiments, the pharmaceutical composition of the disclosure may be administered together with at least one anti-tumor agent, such as an anti-PD-1 antibody. In one embodiment, the pharmaceutical composition of the disclosure may be administered with a cytokine (e.g., IL-2 or IL-21), or a co-stimulatory antibody (e.g., an anti-CD137 antibody or an anti-GITR antibody). In another embodiment, the pharmaceutical composition of the disclosure may be administered with a chemotherapeutic agent, such as a cytotoxin. The subject may be a mammal, especially human.

The PD-L1 associated disease may be an infectious disease, especially a chronic infectious disease. In certain embodiments, the disease may be a chronic viral infection, such as a chronic infection of hepatitis B virus (HBV), hepatitis C virus (HCV), human immunodeficiency virus (HIV), or simian immunodeficiency virus (SIV). In certain embodiments, the pharmaceutical composition of the disclosure may be administered with at least one anti-virus agent. The subject may be a mammal, especially human.

In another aspect, the disclosure provides a method for enhancing an immune response in a subject in need thereof, comprising administering to the subject a therapeutically effective amount of the pharmaceutical composition of the disclosure. The immune response enhancement includes immune cell activation, e.g., T cell activation. The subject may be a mammal, especially human.

Other features and advantages of the instant disclosure will be apparent from the following detailed description and examples, which should not be construed as limiting. The contents of all references, Genbank entries, patents and published patent applications cited throughout this application are expressly incorporated herein by reference.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

BRIEF DESCRIPTION OF THE DRAWINGS

The following detailed description, given by way of example, but not intended to limit the invention solely to the specific embodiments as described, may best be understood in conjunction with the accompanying drawings.

6

Figure 1:
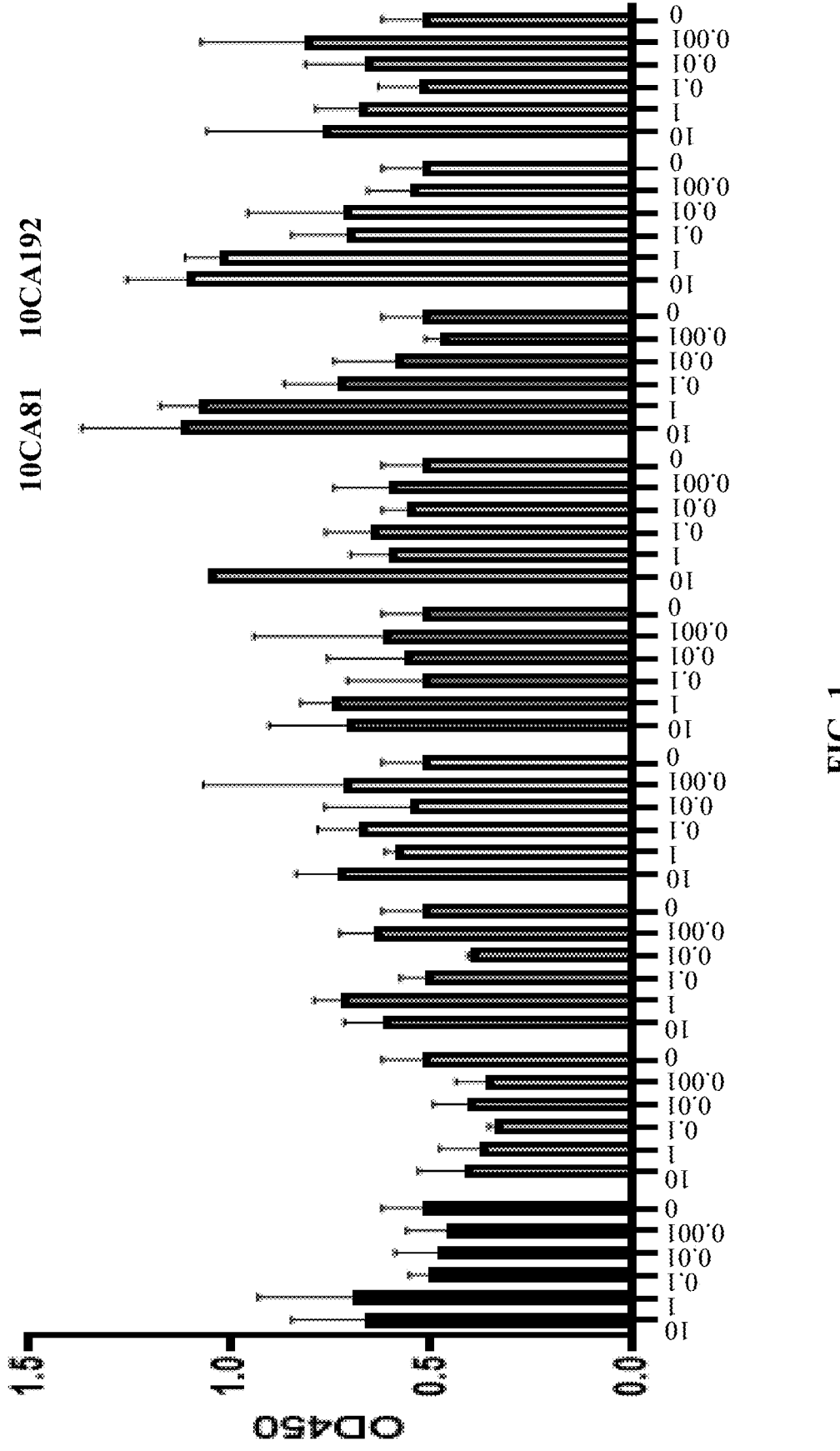

FIG. 1 shows the capability of nine camelid anti-PD-L1 sdAb-Fc fusion proteins, including those comprising the sdAbs 10CA81 and 10CA192, to induce APC-mediated IFN-γ secretion by T cells.

Figure 2:
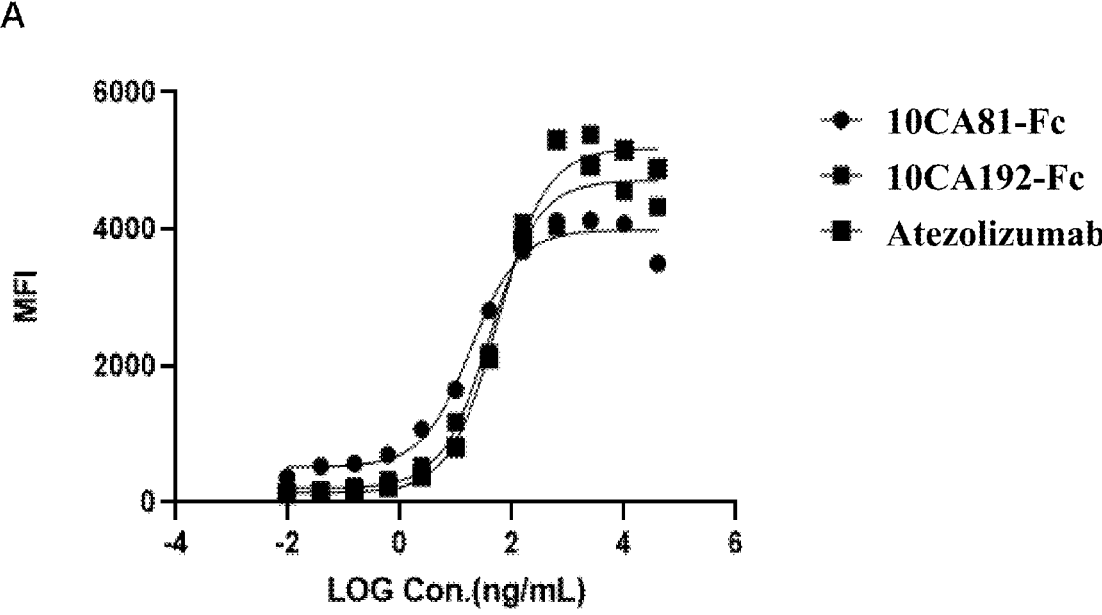
Figure 2:
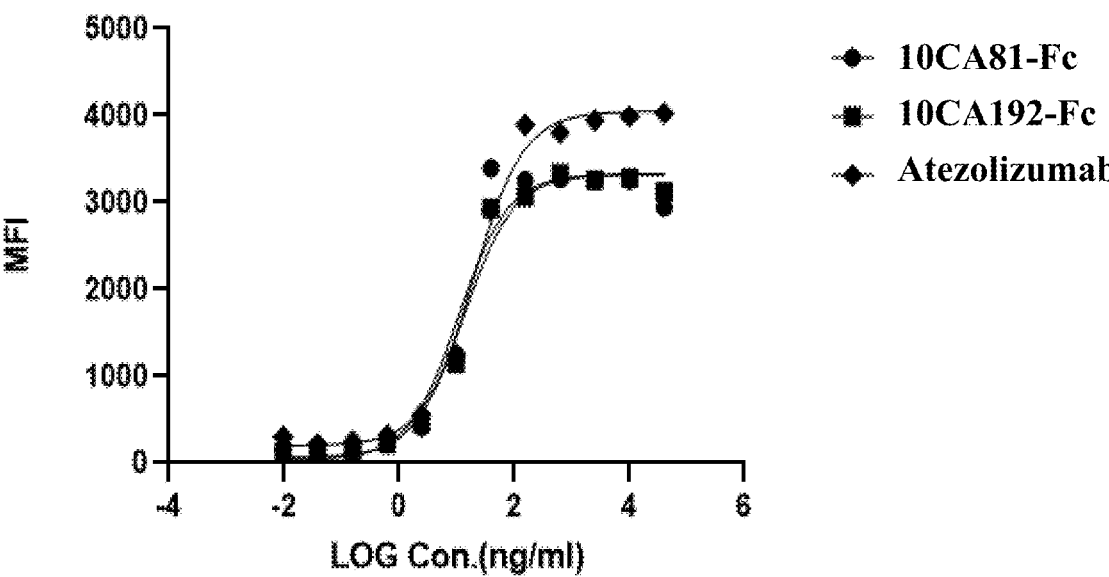

FIG. 2 shows the binding activity of the camelid anti-PD-L1 sdAb-Fc fusion proteins to HEK293A/human PD-L1 cells (A) and HEK293/monkey PD-L1 cells (B).

Figure 3:
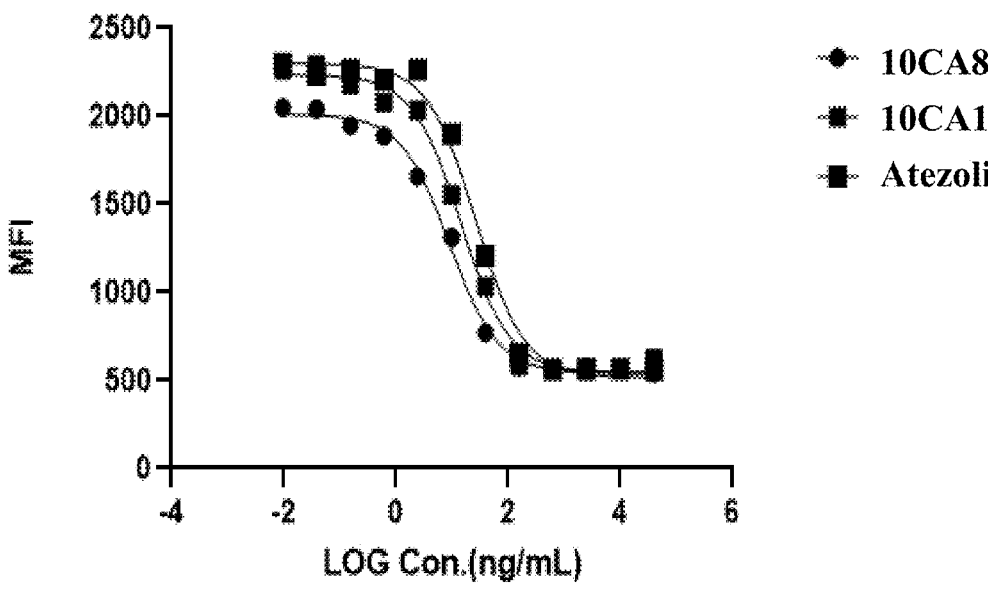

FIG. 3 shows the blocking activity of the camelid anti-PD-L1 sdAb-Fc fusion proteins on PD-L1-PD-1 binding/interaction.

Figure 4:
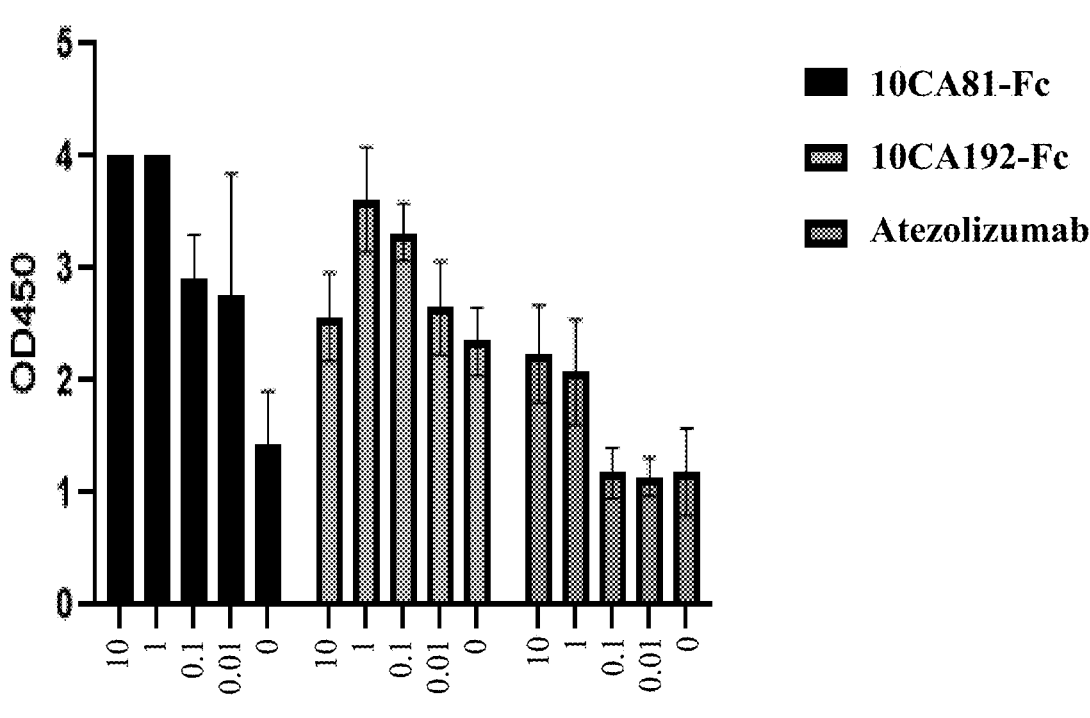

FIG. 4 shows the ability of the camelid anti-PD-L1 sdAb-Fc fusion proteins to induce APC-mediated IFN-γ secretion by T cells.

Figure 5:
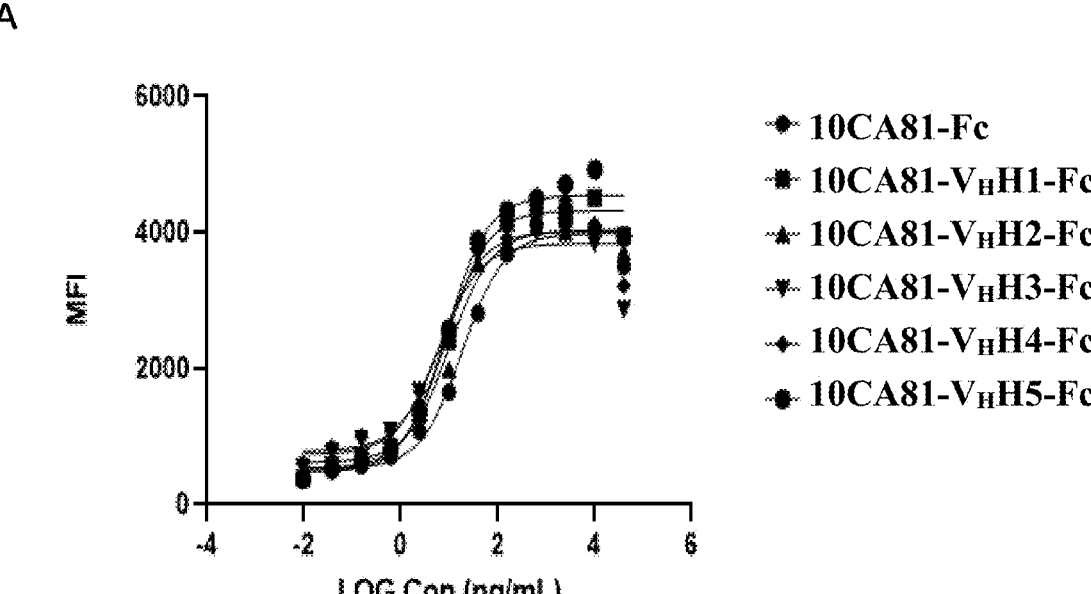
Figure 5:
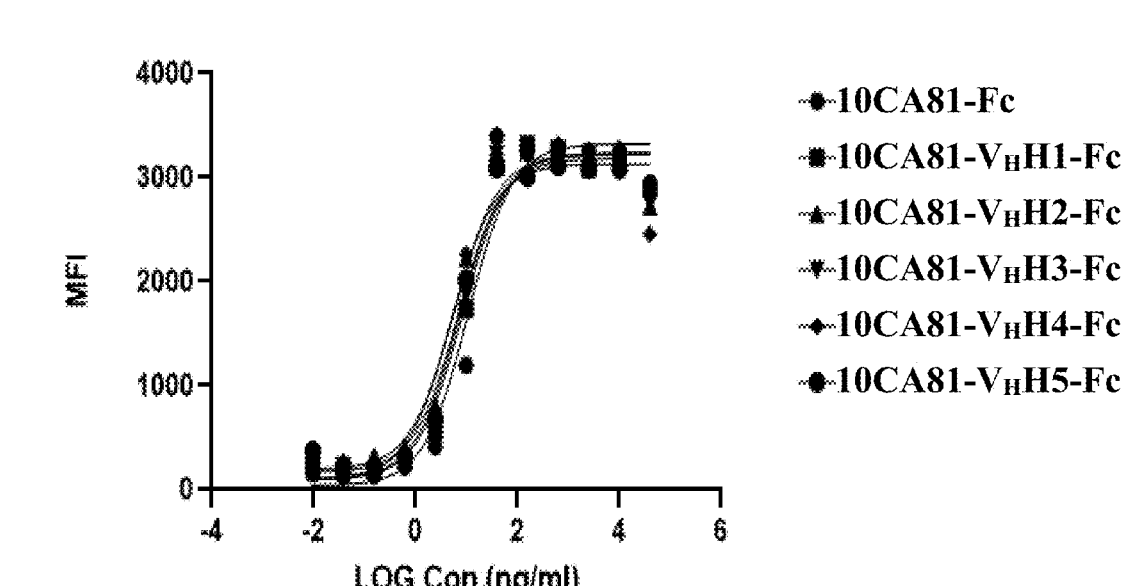

FIG. 5 shows the binding activity of the humanized anti-PD-L1 sdAb (10CA81)-Fc fusion proteins to HEK293A/human PD-L1 cells (A) and HEK293/monkey PD-L1 cells (B).

Figure 6:
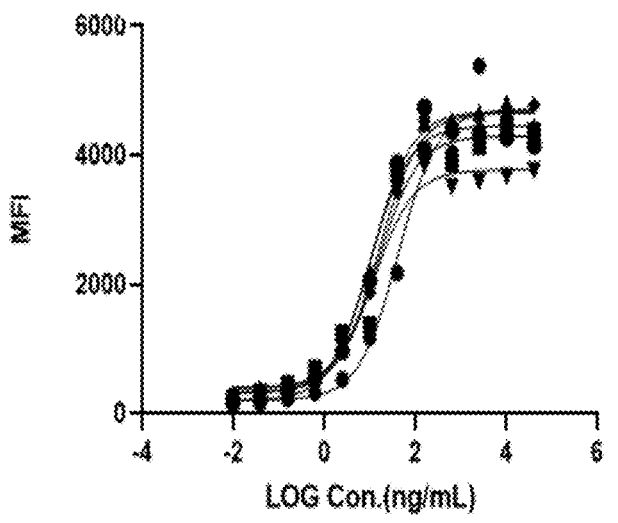
Figure 6:
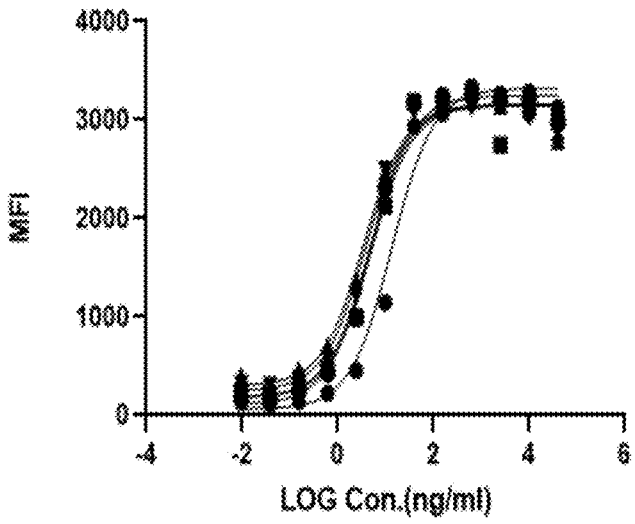

FIG. 6 shows the binding activity of the humanized anti-PD-L1 sdAb (10CA192)-Fc fusion proteins to HEK293A/human PD-L1 cells (A) and HEK293/monkey PD-L1 cells (B).

Figure 7:
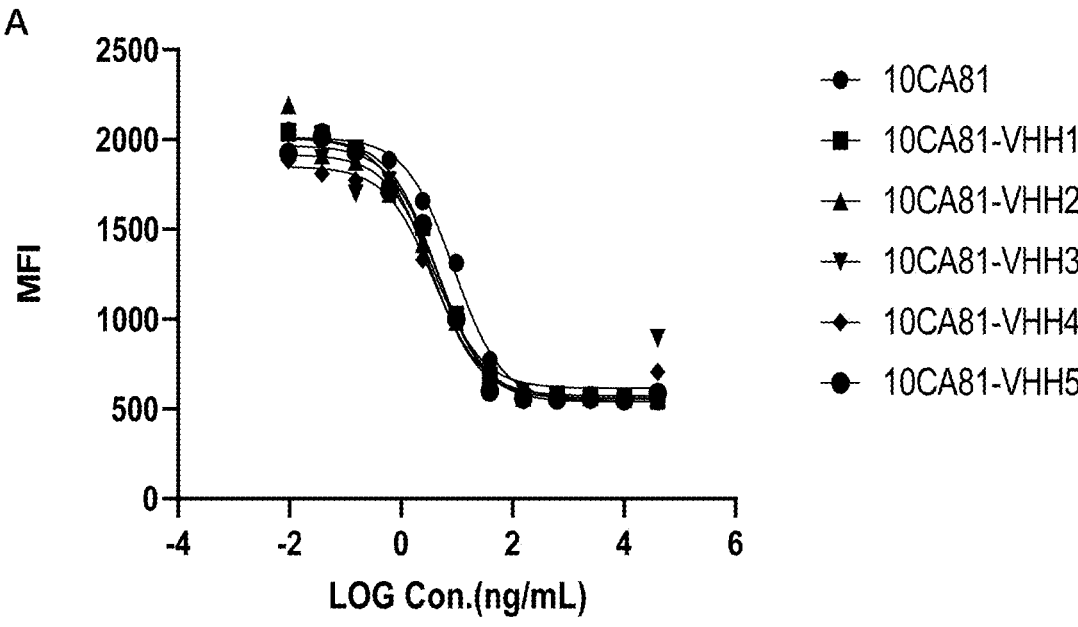
Figure 7:
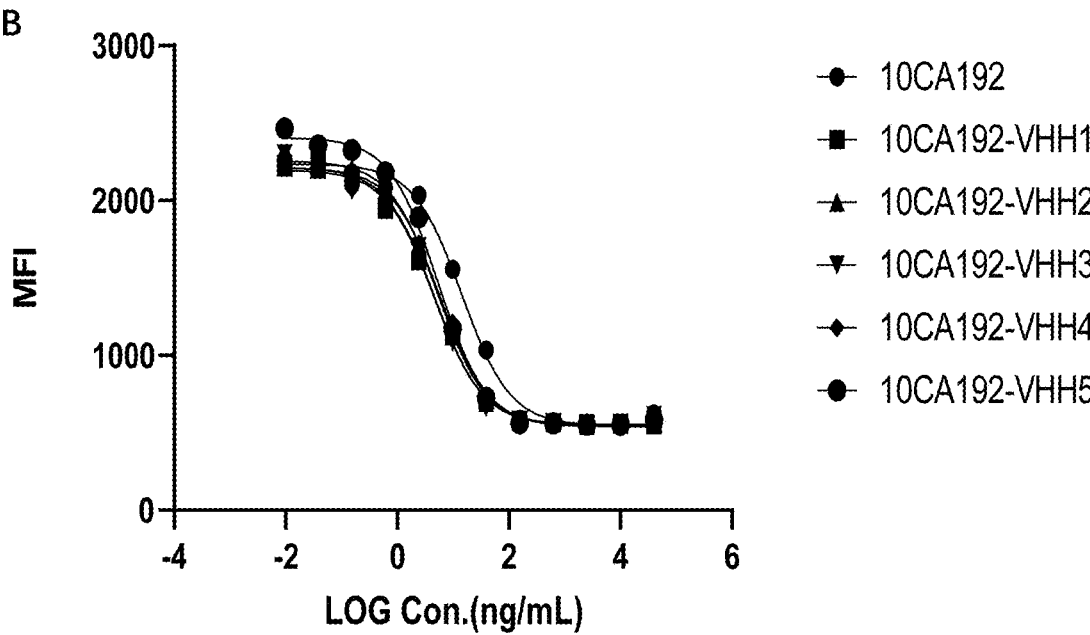

FIG. 7 shows the blocking activity of the humanized anti-PD-L1 sdAb (10CA81)-Fc fusion proteins (A) and the humanized anti-PD-L1 sdAb (10CA192)-Fc fusion proteins (B) on PD-L1-PD-1 binding/interaction.

Figure 8:
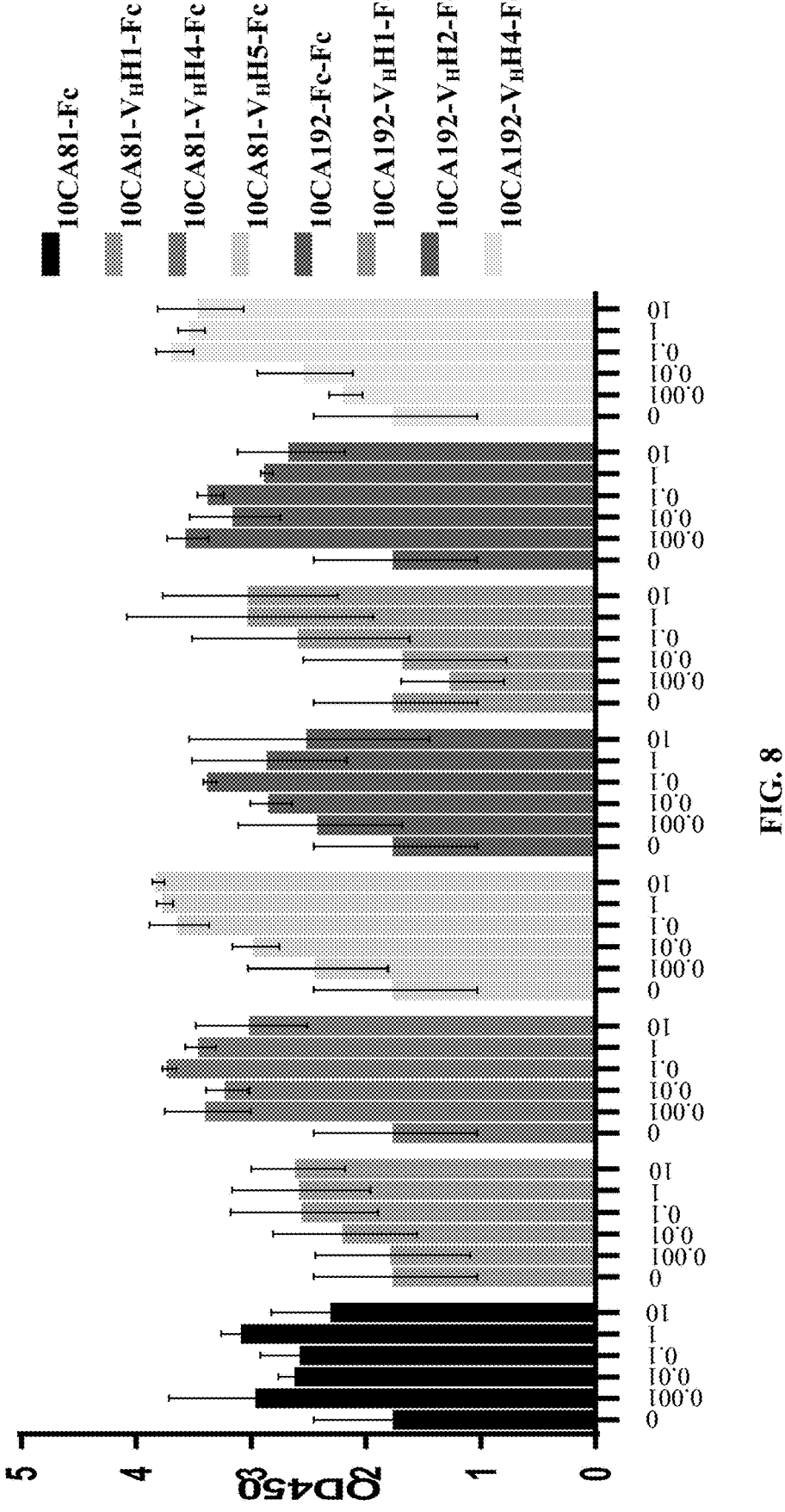

FIG. 8 shows the ability of the humanized anti-PD-L1 sdAb-Fc fusion proteins to induce APC-mediated IFN-γ secretion by T cells.

Figure 9:
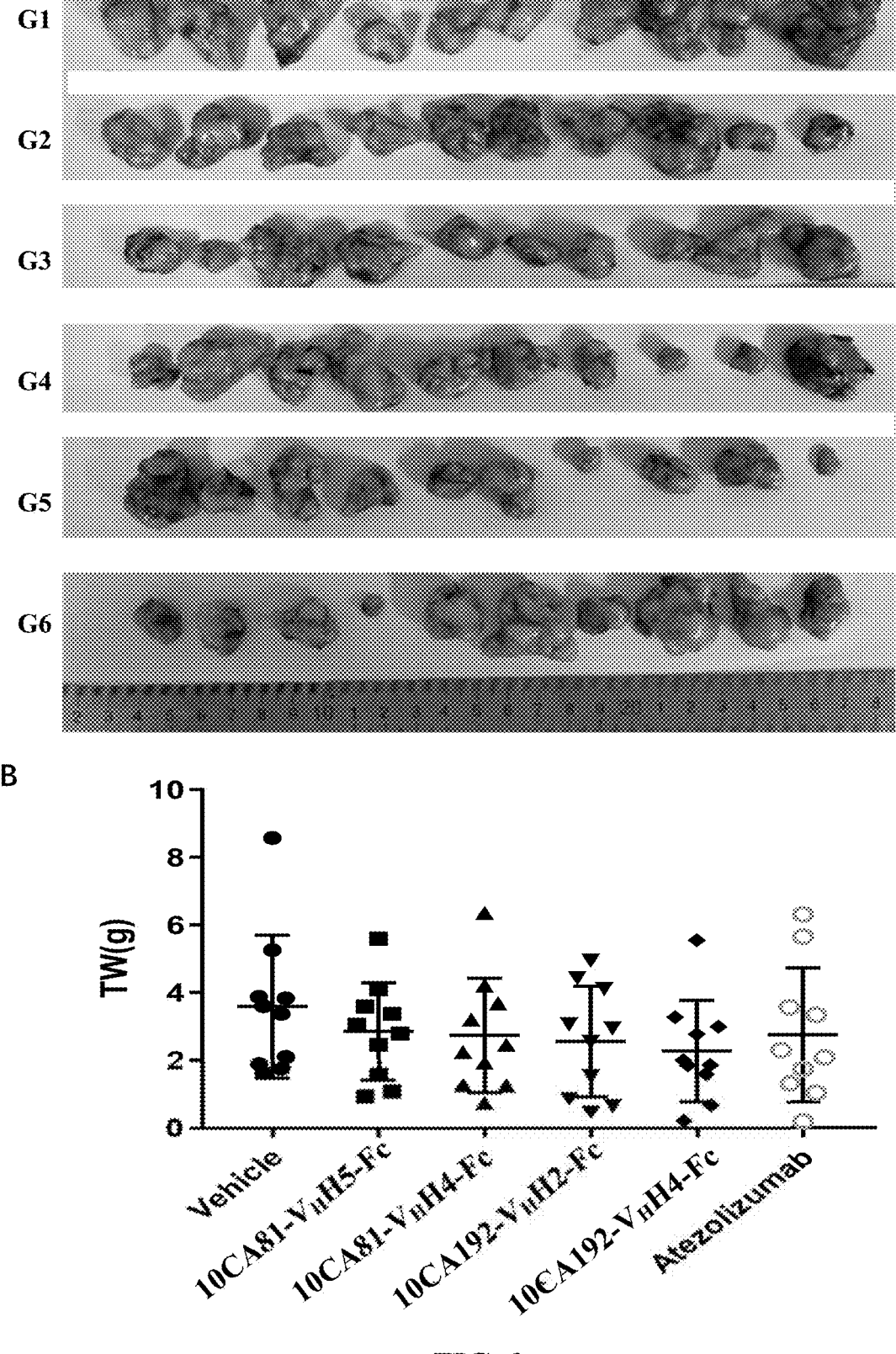

FIG. 9 shows the tumors (A) and tumor weights (B) of tumor-bearing mice treated with the sdAb-Fc fusion proteins of the disclosure or atezolizumab.

DETAILED DESCRIPTION OF THE INVENTION

To ensure that the present disclosure may be more readily understood, certain terms are first defined. Additional definitions are set forth throughout the detailed description.

The term "PD-L1" refers to programmed death-ligand 1, the ligand of programmed death-1 (PD-1). The term comprises variants, isoforms, homologs, orthologs and paralogs. For example, an antibody specific for a human PD-L1 protein may, in certain cases, cross-react with a PD-L1 protein from a species other than human, such as monkey. In other embodiments, an antibody specific for a human PD-L1 protein may be completely specific for the human PD-L1 protein and exhibit no cross-reactivity to other species or of other types, or may cross-react with PD-L1 from certain other species but not all other species.

The term "human PD-L1" refers to a PD-L1 protein having an amino acid sequence from human, such as the amino acid sequence of SEQ ID NO: 11. The term "monkey PD-L1" refers to a PD-L1 protein having an amino acid sequence from a monkey, such as the amino acid sequence of SEQ ID NO: 12. The term "mouse PD-L1" refers to a PD-L1 protein having an amino acid sequence from a mouse, such as the amino acid sequence of SEQ ID NO: 13.

The term "antibody" herein refers to an immunoglobulin that specifically recognizes and binds an antigen through the antigen binding site located in the variable regions of the immunoglobulin, or an antigen binding fragment thereof.

In certain embodiments, the term "antibody" refers to a heavy chain only antibody or an antigen binding fragment thereof. The term "heavy chain only antibody" or "HCAb" refers to a functional antibody, which comprises heavy chains only, but lacks the light chains usually found in 4-chain immunoglobulins. The naturally occurring heavy chain only antibodies are found in e.g., camelids (such as camels, llamas, or alpacas). Each camelid heavy chain only antibody contains a heavy chain variable region/domain, called $V_HH$ domain, $V_HH$ fragment or single-chain antibody (sdAb), and a heavy chain constant region. The $V_HH$ functions to interact with the antigen. The $V_HH$ contains three complementarity determining regions (CDRs) and four framework regions (FRs), arranged from amino-terminus to carboxy-terminus in the following order: FR1, CDR1, FR2, CDR2, FR3, CDR3, FR4. The heavy chain constant region may contain a hinge region, a $C_{H2}$ domain and a CH3 domain. The lacking $C_{H1}$ domain is replaced with an extended hinge region. In a chimeric or humanized heavy chain only antibody, the heavy chain constant region may contain a typical IgG, such as IgG1, IgG2 or IgG4, constant region. The constant region may mediate the binding of the heavy chain only antibody to host tissues or factors, including various cells of the immune system (e.g., effector cells) and the first component (C1q) of the classical complement system. The "functional fragment" of a heavy chain constant region refers to the part of the constant region that retains certain activity such as the binding affinity to FcRs and/or the complement system component(s).

The "antigen binding fragment" or "antigen binding portion" as used in connection with a heavy chain only antibody refers to one or more fragments of a heavy chain only antibody that retain the ability to specifically bind to an antigen (e.g., PD-L1). It has been shown that the antigen-binding function of a heavy chain antibody can be performed by fragments of a full-length heavy chain only antibody. Examples of "antigen-binding fragments/portions of a heavy chain only antibody include, but not limited to, (i) an isolated complementarity determining region (CDR); (ii) a monovalent $V_HH$ fragment; (iii) a bivalent fragment comprising two monovalent $V_HH$ fragments; (iv) a monovalent fragment comprising a $V_HH$ fragment linked to a partial heavy chain constant region, such as a $V_HH$ domain linked to the $C_{H2}$ domain, or $C_{H2}$ and $C_{H3}$ domains of a heavy chain constant region; (v) a bivalent fragment comprising two $V_HH$ fragments each linked to a partial heavy chain constant region; (vi) multiple monovalent $V_HH$ domains (each with or without a full or partial heavy chain constant region) linked with or without linkers.

In certain embodiments, the term "antibody" refers to a single-domain antibody, or a nanobody. The term "single-domain antibody", "nanobody" or "sdAb" refers to a single antigen-binding polypeptide comprising a single monomeric variable antibody domain having three complementary determining regions (CDRs), which is capable of binding to an antigen without pairing with a corresponding CDR-containing polypeptide. In some cases, the single domain antibody is engineered from a camelid HCAb, and is also called the $V_HH$ domain or fragment of the HCAb. The single domain antibody is a kind of antigen-binding portion of a heavy chain only antibody. Camelid sdAb is one of the smallest known antigen binding antibody fragments.

The term "Fc region" of an antibody, including a heavy chain antibody, is the tail region of an antibody that interacts with Fc receptors and some proteins of the complement system to activate the immune system. The IgG, IgA and IgD Fc region is composed of two identical fragments derived from the second and third constant domains ($C_{H2}$ and $C_{H3}$) of the antibody's heavy chains, while the IgM and IgB Fc regions contain three heavy chain constant domains ($C_H$ domains 2-4), The Fc region may bind to the complement component C1q to activate the classical complement cascade, may bind to the Fc receptors on phagocytes (i.e., macrophages, granulocytes and dendritic cells) to induce phagocytosis of cells bound by the antibodies, may bind to the Fc receptors of immune effector cells (mainly natural killer cells) to induce release of cytotoxic granules from the immune effector cells, which cause the death of the antibody-coated cells, and may bind to the Fc receptor of the antigen-presenting cells such as dendritic cells to induce humoral and cellular immune responses.

The term "camelid antibody", as used herein, is intended to include antibodies having variable regions (or more specifically the $V_HH$ fragments) in which both the framework and CDR regions are derived from camelid germline heavy chain only antibody sequences. Furthermore, if the antibody contains a constant region, the constant region also is derived from camelid germline antibody sequences. The camelid antibodies of the disclosure can include amino acid residues not encoded by camelid germline antibody sequences (e.g., mutations introduced by random or site-specific mutagenesis in vitro or by somatic mutation in vivo). However, the term "camelid antibody", as used herein, is not intended to include antibodies in which CDR sequences derived from the germline of another mammalian species have been grafted onto camelid framework sequences.

The term "chimeric antibody" refers to an antibody made by combining genetic material from a nonhuman (e.g., camelid) source with genetic material from a human being. Or more generally, a chimeric antibody is an antibody having genetic material from a certain species with genetic material from another species.

The term "humanized antibody", as used herein, refers to an antibody from non-human (e.g., camelid) species whose protein sequences have been modified to increase similarity to antibody variants produced naturally in humans.

As used herein, an antibody that "specifically binds to human PD-L1" is intended to refer to an antibody that binds to human PD-L1 protein (and possibly a PD-L1 protein from one or more non-human species) but does not substantially bind to non-PD-L1 proteins. Preferably, the antibody binds to human PD-L1 protein with "high affinity", namely with a Ko of $5.0 \times 10^{-9}$ M or less.

The percent "sequence identity" as used herein in the context of two or more nucleic acids or polypeptides, refers to two or more sequences or subsequences that are the same or have a specified percentage of nucleotides or amino acid residues that are the same, when compared and aligned (introducing gaps, if necessary) for maximum correspondence, considering or not considering conservative amino acid substitutions as part of the sequence identity. The percent identity can be measured using sequence comparison software or algorithms or by visual inspection. Various algorithms and software that can be used to obtain alignments of amino acid or nucleotide sequences are well-known in the art. These include, but are not limited to, BLAST, ALIGN, Megalign®, BestFit, GCG Wisconsin Package, and variants thereof. In some embodiments, two nucleic acids or polypeptides of the disclosure are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection.

The term "$EC_{50}$", also known as half maximal effective concentration, refers to the concentration of a molecule, e.g., an antibody, which induces a response halfway between the baseline and maximum after a specified exposure time.

The term "IC$_{50}$", also known as half maximal inhibitory concentration, refers to the concentration of a molecule, e.g., an antibody, which inhibits a specific biological or biochemical function by 50% relative to the absence of the molecule.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount of a molecule, e.g., an antibody, of the present disclosure sufficient to prevent or ameliorate the symptoms associated with a disease or condition (such as a cancers) and/or lessen the severity of the disease or condition. A therapeutically effective amount is understood to be in context to the condition being treated, where the actual effective amount is readily discerned by those of skill in the art.

Various aspects of the disclosure are described in further detail as follows.

The molecule (also referred to as PD-L1 binding molecule herein) of the disclosure, including the single-domain antibody, the heavy chain only antibody or the antigen binding fragment thereof, may specifically bind human and monkey PD-L1 molecules with the binding activity/affinity comparable to or higher than that of the prior art antibodies such as atezolizumab. Further, as compared to the prior art antibodies such as atezolizumab, the molecule of the disclosure, including the single-domain antibody, the heavy chain only antibody or the antigen binding fragment thereof, has i) comparable, if not higher blocking activity on PD-1-PD-L1 interaction, ii) comparable, if not higher activity on T cell activation, and/or iii) comparable, if not higher, in vivo anti-tumor efficacy.

The preferable single-domain antibody and/or heavy chain only antibody of the disclosure is/are monoclonal. The single-domain antibody may be e.g., camelid or humanized. The heavy chain only antibody may be e.g., camelid, chimeric or humanized.

The variable region CDRs in molecule of the disclosure, including the single-domain antibody, the heavy chain only antibody or the antigen binding fragment thereof, have been defined by the Kabat numbering system. However, as is well known in the art, the CDRs can also be determined by other systems such as Chothia, and IMGT, AbM, or Contact numbering system/method, based on variable region sequence.

The SEQ ID NOs of the variable region and the CDR sequences in the molecule of the disclosure, including the single-domain antibody, the heavy chain only antibody or the antigen binding fragment thereof, are summarized in Table 1.

TABLE 1

| SEQ ID NOs of CDR and variable region sequences | | | | |
| --- | --- | --- | --- | --- |
| mAb ID | CDR1 | CDR2 | CDR3 | V$_H$H |
| 10CA81 | SEQ ID | SEQ ID | SEQ ID | SEQ ID NO: 4 |
| 10CA81-V$_H$H4 | NO: 1 | NO: 2, | NO: 3, | SEQ ID NO: 5 |
| 10CA81-V$_H$H5 | | X1 = T, B = N, | X = K | SEQ ID NO: 6 |
| | | X2 = A | | |

TABLE 1-continued

| SEQ ID NOs of CDR and variable region sequences | | | | |
| --- | --- | --- | --- | --- |
| mAb ID | CDR1 | CDR2 | CDR3 | V$_H$H |
| 10CA192 | SEQ ID | SEQ ID | SEQ ID | SEQ ID NO: 7 |
| 10CA192-V$_H$H2 | NO: 1 | NO: 2, | NO: 3, | SBQ ID NO: 8 |
| 10CA192-V$_H$H4 | | X1 = L, B = D, | X = A | SEQ ID NO: 9 |
| | | X2 = V | | |

The single-domain antibody may be linked to, and/or the PD-L1-binding molecule of the disclosure may contain a heavy chain constant region, such as IgG1 constant region, or a functional fragment thereof. In certain embodiments, the heavy chain constant region may be human IgG1 constant region (the Fc region) comprising the amino acid sequence of SEQ ID NO: 10. The heavy chain constant region may be with enhanced FcR binding affinity.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al., *J. Mol. Biol,* 296:833-849 (2000); Rader et al., *Proc. Natl. Acad. Sci. U.S.A.* 95:8910-8915 (1998); Barbas et al., *J. Am, Chem, Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIAjournal* 8: *Scientific Review* 8 (2001); Igarashi et al., *J. Biochem* (Tokyo) 117:452-7 (1995); Bourgeois et al., *J. Virol* 72:807-10 (1998); Levi et al., *Proc. Natl. Acad. Sci. U.S.A.* 90:4374-8 (1993); Polymenis and Stoller, *J. Immunol.* 152: 5218-5329 (1994) and Xu and Davis, Immunity 13:37-45 (2000).

The PD-L1 binding molecule of the disclosure, including the single-domain antibody, the heavy chain only antibody or the antigen binding fragment thereof, may comprise the CDR3 of the heavy chain variable region of the disclosure and the CDRs, such as CDR1 and/or CDR2, from other single-domain or heavy chain only antibodies specifically binding human PD-L1. Preferably these antibodies (a) compete for binding with PD-L1; (b) retain the functional characteristics; (c) bind to the same epitopes and/or (d) have a similar binding affinity as the PD-L1-binding molecule of the present disclosure.

In another embodiment, the PD-L1 binding molecule of the disclosure, including the single-domain antibody, the heavy chain only antibody or the antigen binding fragment thereof; may comprise a heavy chain variable region sequence or CDR1, CDR2 and CDR3 sequences which differ from those of the PD-L1 binding molecule of the disclosure, including the single-domain antibody, the heavy chain only antibody or the antigen binding fragment thereof. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.* 32:6862-35; Adib-Conquy et al., (1998) *Int. Immunol.* 10:341-6 and Beers et al., (2000) *Clin. Can. Res.* 6:2835-43.

Accordingly, in one embodiment, the PD-L1 binding molecule of the disclosure, including the single-domain antibody, the heavy chain only antibody or the antigen binding fragment thereof, may comprise a heavy chain variable region comprising CDR1, CDR2, and CDR3 sequences, wherein;

(a) the heavy chain variable region CDR1 sequence comprises a sequence listed in Table 1 above, and/or conservative modifications thereof; and/or (b) the heavy chain variable region CDR2 sequence comprises a sequence listed in Table 1 above, and/or conservative modifications thereof; and/or (c) the heavy chain variable region CDR3 sequence comprises a sequence listed in Table 1 above, and conservative modifications thereof; and (e) the PD-L1 binding molecule specifically binds human PD-L1.

The molecule of the disclosure, including the single-domain antibody, the heavy chain only antibody or the antigen binding fragment thereof may possess one or more of the following functional properties, such as high binding affinity and specificity to human PD-L1, high blocking activity on PD-1-PD-L1 interaction, high capability to activate T cells, and high in vivo anti-tumor efficacy.

In various embodiments, the single-domain antibody of the disclosure may be, for example, camelid, or humanized, and the heavy chain only antibody of the disclosure may be, for example, camelid, chimeric or humanized.

As used herein, the term "conservative sequence modification" is intended to refer to amino acid modifications that do not significantly affect or alter the binding characteristics of the antibody or the molecule containing the amino acid sequence. Such conservative modification includes amino acid substitutions, additions and deletions. Modifications can be introduced into the PD-L1 binding molecule of the disclosure, including the single-domain antibody, the heavy chain only antibody or the antigen binding fragment thereof, by standard techniques known in the art, such as site-directed mutagenesis and PCR-mediated mutagenesis. Conservative amino acid substitutions are ones in which an amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody or a PD-L1-binding molecule of the disclosure may be replaced with other amino acid residues from the same side chain family and the altered antibody or molecule may be tested for retained function (i.e., the functions set forth above) using the functional assays described herein.

The molecule of the disclosure, including the single-domain antibody, the heavy chain only antibody or the antigen binding fragment thereof, can be prepared using the PD-L1-binding molecule of the disclosure having the $V_HH$ sequences of the present disclosure as starting material. The molecule of the disclosure, including the single-domain antibody, the heavy chain only antibody or the antigen binding fragment thereof, can be engineered by modifying one or more residues within the variable region (i.e., $V_HH$), for example within one or more CDRs and/or within one or more framework regions. Additionally or alternatively, a PD-L1-binding molecule may be engineered by modifying residues within the constant region(s), for example to alter the effector function(s).

In certain embodiments, CDR grafting can be used to engineer the variable region of molecule of the disclosure, including the single-domain antibody, the heavy chain only antibody or the antigen binding fragment thereof. The PD-L1-binding molecule of the disclosure interacts with the target antigen predominantly through amino acid residues that are located in the (heavy chain) complementarity determining regions (CDRs). For this reason, the amino acid sequences within the CDRs are more diverse between individual antibodies than sequences outside of the CDRs. Because the CDR sequences are responsible for most antibody-antigen interactions, it is possible to express recombinant antibodies that mimic the properties of specific naturally occurring antibodies by constructing expression vectors that include the CDR sequences from the specific naturally occurring antibody grafted onto framework sequences from a different antibody with different properties (see, e.g., Riechmann et al., (1998) *Nature* 332:323-327; Jones et al., (1986) *Nature* 321:522-525; Queen et al., (1989) *Proc. Natl. Acad. See also U.S.A.* 86:10029-10033; U.S. Pat. Nos. 5,225,539; 5,530,101; 5,585,089; 5,693,762 and 6,180, 370).

Accordingly, another embodiment of the disclosure pertains to an isolated molecule of the disclosure, including the single-domain antibody, the heavy chain only antibody or the antigen binding fragment thereof, comprising a heavy chain variable region ($V_HH$) comprising CDR1, CDR2, and CDR3 sequences comprising the sequences of the present disclosure, as described above. While these molecules contain the $V_HH$ CDR sequences of the present disclosure, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al., (1991), cited supra; Tomlinson et al., (1992) *J. Mol. Biol.* 227:776-798; and Cox et al., (1994) *Eur. J. Immunol.* 24:827-836. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG-0010109, NT-024637 & BC070333), 3-33 (NG-0010109 & NT-024637) and 3-7 (NG-0010109 & NT-024637). As another example, the following heavy chain germline sequences found in the HCo12 HuMAb mouse are available in the accompanying Genbank Accession Nos.: 1-69 (NG-0010109, NT-024637 & BC070333), 5-51 (NG-0010109 & NT-024637), 4-34 (NG-0010109 & NT-024637), 3-30.3 (CAJ556644) & 3-23 (AJ406678).

The molecule (including the single-domain antibody, the heavy chain only antibody or the antigen binding fragment thereof) sequences are compared against a compiled protein sequence database using one of the sequence similarity searching methods called the Gapped BLAST (Altschul et al., (1997), supra), which is well known to those skilled in the art.

Preferred framework sequences for use in the molecule of the disclosure, including the single-domain antibody, the heavy chain only antibody or the antigen binding fragment thereof, are those that are structurally similar to the framework sequences used by the molecule of the disclosure, including the single-domain antibody, the heavy chain only antibody or the antigen binding fragment thereof. The $V_HH$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the molecule (see e.g., U.S. Pat. Nos. 5,530,101; 5,585,089; 5,693,762 and 6,180,370).

Another type of variable region modification is to mutate amino acid residues within the $V_HH$ CDR1, CDR2 and/or CDR3 regions to thereby improve one or more binding properties (e.g., affinity) of the molecule of interest. Site-directed mutagenesis or PCR-mediated mutagenesis can be performed to introduce the mutation(s) and the effect on antigen binding, or other functional property of interest, can be evaluated in in vitro or in vivo assays as known in the art. The mutations can be amino acid substitutions, additions or deletions, but are preferably substitutions. Moreover, typically no more than one, two, three, four or five residues within a CDR region are altered.

Accordingly, in another embodiment, the disclosure provides an isolated molecule of the disclosure, including the single-domain antibody, the heavy chain only antibody or the antigen binding fragment thereof, comprising a heavy chain variable region comprising: (a) a $V_HH$ CDR1 comprising the sequence of the present disclosure, or an amino acid sequence having one, two, three, four or five amino acid substitutions, deletions or additions; (b) a $V_HH$ CDR2 comprising the sequence of the present disclosure, or an amino acid sequence having one, two, three, four or five amino acid substitutions, deletions or additions; and (e) a $V_HH$ CDR3 comprising the sequence of the present disclosure, or an amino acid sequence having one, two, three, four or five amino acid substitutions, deletions or additions.

Engineered molecules of the disclosure include those in which modifications have been made to framework residues within the $V_HH$, e.g. to improve the properties of the molecules. The modification may involve mutating one or more residues within the framework region, or even within one or more CDRs, to remove T cell epitopes to thereby reduce the potential immunogenicity of the molecule. This approach is also referred to as "deimmunization" and is described in further detail in U.S. Patent Publication No. 20030153043.

In addition, or as an alternative to modifications made within the framework or CDRs, the molecules of the disclosure, especially the heavy chain only antibodies of the disclosure, may be engineered to include modifications within the Fc region, typically to alter one or more functional properties of the molecule, such as serum half-life, complement fixation, Fc receptor binding, and/or antigen-dependent cellular cytotoxicity. Furthermore, a molecule of the disclosure can be chemically modified (e.g., one or more chemical moieties can be attached to the molecule) or be modified to alter its glycosylation, again to alter one or more functional properties of the molecule.

In one embodiment, the hinge region besides the Cin is modified in such that the number of cysteine residues in the hinge region is altered, e.g., increased or decreased. This approach is described further in U.S. Pat. No. 5,677,425. The number of cysteine residues in the hinge region is altered to, for example, facilitate assembly of the heavy chains or to increase or decrease the stability of the molecules.

In another embodiment, the Fc hinge region of a heavy chain only antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In still another embodiment, the glycosylation of a molecule of the disclosure, including the single-domain antibody, the heavy chain only antibody or the antigen binding fragment thereof, is modified. For example, a glycosylated molecule can be made (i.e., the molecule lacks glycosylation). Glycosylation can be altered to, for example, increase the affinity of the molecule for the antigen. Such carbohydrate modifications can be accomplished by, for example, altering one or more sites of glycosylation within the molecule sequence. For example, one or more amino acid substitutions can be made that result in elimination of one or more variable region framework glycosylation sites to thereby eliminate glycosylation at that site. Such aglycosylation may increase the affinity of the molecule for antigen. See, e.g., U.S. Pat. Nos. 5,714,350 and 6,350,861.

Additionally or alternatively, a molecule can be made that has an altered type of glycosylation, such as a hypofucosylated molecule having reduced amounts of fucosyl residues or a molecule having increased bisecting GlcNac structures. Such altered glycosylation patterns have been demonstrated to increase the ADCC as induced by the molecules. Such carbohydrate modifications can be accomplished by, for example, expressing the molecule in a host cell with altered glycosylation machinery. Cells with altered glycosylation machinery have been described in the art, including, but not limited to, cell lines lacking FUT8, Lec13 (a variant CHO cell line), YB2/0 (a rat hybridoma cell line), cell lines containing small interfering RNAs specifically against Fut8 gene, and cell lines co-expressing 1,4-N-acetyl-glucosamine transferase III and Golgi alpha-mannosidase II. These cells may be used as the host cells for expressing the recombinant molecules of the disclosure, to thereby produce molecules with altered glycosylation.

Another modification of the molecules is pegylation. A molecule can be pegylated to, for example, increase the biological (e.g., serum) half-life of the molecule. To pegylate a molecule, the molecule typically is reacted with polyethylene glycol (PEG), such as a reactive ester or aldehyde derivative of PEG, under conditions in which one or more PEO groups become attached to the molecule. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the molecule to be pegylated is an aglycosylated molecule. Methods for pegylating proteins are known in the art and can be applied to the molecules of the disclosure. See, e.g., EPO 154 316 and EP 0 401 384.

The molecule of the disclosure, including the single-domain antibody, the heavy chain only antibody or the antigen binding fragment thereof, can be characterized by its various physical properties, to detect and/or differentiate different classes thereof.

For example, the molecules of the disclosure may contain one or more glycosylation sites in the heavy chain variable region. Such glycosylation sites may result in increased immunogenicity of the molecule or an alteration of the pK of the molecule due to altered antigen binding (Marshall et al (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al., (2000) *Mol Immunol* 37:697-706). Glycosylation has been known to occur at motifs containing an N-X-S/T sequence. In some instances, it is preferred to have a molecule of the disclosure that does not contain variable region glycosylation. This can be achieved either by selecting molecules that do not contain the glycosylation motif in the variable region or by mutating residues within the glycosylation region.

In a preferred embodiment, the molecules of the disclosure do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-PD-L1 antibody that contains a pI value that falls in the normal range. This can be achieved either by selecting antibodies with a pI in the normal range or by mutating charged surface residues.

In another aspect, the disclosure provides nucleic acid molecules that encode the variable region, CDRs and/or other fragments of the s molecule of the disclosure, including the single-domain antibody, the heavy chain only antibody or the antigen binding fragment thereof. The nucleic acid molecules can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the disclosure can be, e.g., DNA or RNA and may or may not contain intronic sequences. In a preferred embodiment, the nucleic acid is a cDNA molecule.

The nucleic acid molecule of the disclosure can be obtained using standard molecular biology techniques. For the molecules expressed by hybridomas (e.g., hybridomas prepared from camels), cDNAs encoding the heavy chains of the molecule made by the hybridoma can be obtained by standard PCR amplification or cDNA cloning techniques. For the molecules obtained from an immunoglobulin gene library (e.g., using phage display techniques), a nucleic acid encoding such molecules can be recovered from the gene library.

Preferred nucleic acids molecules of the disclosure include those encoding the $V_H H$ sequences or the CDRs of the molecule of the disclosure, including the single-domain antibody, the heavy chain only antibody or the antigen binding fragment thereof. Once DNA fragments encoding $V_H H$ segments are obtained, these DNA fragments can be further manipulated by standard recombinant DNA techniques, for example to convert the variable region genes to full-length heavy chain only antibody chain genes. The term "operatively linked", as used in this context, is intended to mean that the two DNA fragments are joined such that the amino acid sequences encoded by the two DNA fragments remain in-frame.

The isolated DNA encoding the $V_H H$ can be converted to a full-length heavy chain only gene by operatively linking the $V_H H$-encoding DNA to another DNA molecule encoding heavy chain constant regions ($C_{H1}$, $C_{H2}$ and/or $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region.

Monoclonal single-domain or heavy chain only antibodies of the present disclosure can be produced using the well-known somatic cell hybridization (hybridoma) technique of Kohler and Milstein (1975) *Nature* 256: 495. Other embodiments for producing monoclonal antibodies include viral or oncogenic transformation of B lymphocytes and phage display techniques. Chimeric or humanized antibodies, and their preparation, are also well known in the art. See e.g., U.S. Pat. Nos. 4,816,567; 5,225,539; 5,530,101; 5,585,089; 5,693,762 and 6,180,370.

The single-domain or heavy chain only antibodies or the antigen binding fragments thereof of the disclosure can also be produced in a host cell transfectoma using, for example, a combination of recombinant DNA techniques and gene transfection methods as is well known in the art (e.g., Morrison, S. (1985) Science 229:1202). In one embodiment, the DNA fragment encoding partial or full-length heavy chains obtained by standard molecular biology techniques is inserted into the expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology, Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

The DNA fragment encoding heavy chain variable region ($V_H H$) is used to create the full-length heavy chain only antibody genes of any antibody isotype by inserting it into an expression vector already encoding a heavy chain constant region of the desired isotype such that the $V_HH$ segment is operatively linked to the $C_H$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017), For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the heavy chains, the expression vector encoding the heavy chain is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant molecules especially antibodies of the disclosure include cell lines lacking FUT8, Lec13 (a variant CHO cell line), YB2/0 (a rat hybridoma cell line), cell lines containing small interfering RNAs specifically against Fut8 gene, cell lines co-expressing 1,4-N-acetyl-glucosamine transferase III and Golgi alpha-mannosidase II, Chinese Hamster Ovary (CHO cells) (including dhfr– CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. When the recombinant expression vectors encoding antibody genes are introduced into mammalian host cells, the antibodies are produced by culturing the host cells for a period of time sufficient to allow for expression of the antibodies in the host cells or, more preferably, secretion of the antibodies into the culture medium in which the host cells are grown. The antibodies can be recovered from the culture medium using standard protein purification methods.

The molecule of the disclosure, including the single-domain antibody, the heavy chain only antibody or the antigen binding fragment thereof, may be conjugated to a therapeutic agent to form an immunoconjugate such as an antibody-drug conjugate (ADC). Suitable therapeutic agents include cytotoxins, alkylating agents, DNA minor groove binders, DNA intercalators, DNA crosslinkers, histone deacetylase inhibitors, nuclear export inhibitors, proteasome inhibitors, topoisomerase I or II inhibitors, beat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038,658; WO 07/051,081; WO 07/059, 404; WO 08/083,312; and WO 08/103,693; U.S. Patent Publications 20060024317; 20060004081; and 20060247295.

In another aspect, the present disclosure features a bispecific molecule comprising molecule of the disclosure, including the single-domain antibody, the heavy chain only antibody or the antigen binding fragment thereof, linked to at least one other functional molecule, e.g., another peptide or protein (e.g., another antibody or ligand for a receptor) to generate a bispecific molecule that binds to at least two different binding sites or target molecules. Thus, as used herein, the "bispecific molecule" includes molecules that have three or more specificities.

The bispecific molecules may be in many different formats and sizes. At one end of the size spectrum, a bispecific molecule retains the traditional antibody format, except that, instead of having two binding arms of identical specificity, it has two binding arms each having a different specificity, At the other extreme are bispecific molecules consisting of two single-domain antibodies ($V_HHs$) linked by a peptide chain, a so-called $Bs(sdAb)_2$ construct. Bispecific molecules of these and other formats can be prepared by genetic engineering, somatic hybridization, or chemical methods. See, e.g., Kufer et al, cited supra; Cao and Suresh, *Bioconjugate Chemistry,* 9 (6), 635-644 (1998); and van Spriel et al., *Immunology Today,* 21 (8), 391-397 (2000), and the references cited therein.

The disclosure provides a chimeric antigen receptor comprising an anti-PD-L1 single-domain antibody ($V_HH$) of the disclosure.

The chimeric antigen receptor may comprise (a) an extracellular antigen recognition domain containing the anti-PD-L1 $V_HH$, (b) a transmembrane domain, and (c) an intracellular signaling domain.

An oncolytic virus preferentially infects and kills cancer cells. The molecule of the disclosure, including the single-domain antibody, the heavy chain only antibody or the antigen binding fragment thereof, may be used in conjunction with the oncolytic virus. Alternatively, an oncolytic virus encoding molecule of the disclosure, including the single-domain antibody, the heavy chain only antibody or the antigen binding fragment thereof, can be introduced into human bodies.

In another aspect, the present disclosure provides a pharmaceutical composition comprising the molecule of the disclosure (including the single-domain antibody, the heavy chain only antibody or the antigen binding fragment thereof), the immunoconjugate, the bispecific molecule, the immune cell carrying the chimeric antigen receptor, the oncolytic virus, the nucleic acid molecule, the expression vector, and/or the host cell of the present disclosure formulated together with a pharmaceutically acceptable carrier.

The pharmaceutical composition may optionally contain one or more additional pharmaceutically active ingredients, such as an anti-tumor agent, or an agent for immunity enhancement. The pharmaceutical composition of the disclosure may be administered in a combination therapy with, for example, an anti-tumor agent, or an agent for immunity enhancement.

The pharmaceutical composition may comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: *The Science and Practice of Pharmacy,* 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the pharmaceutical composition of the disclosure can be administered via a non-parenteral route, such as a topical, epidermal or mucosal route of administration, e.g., intranasally, orally, vaginally, rectally, sublingually or topically.

The pharmaceutical composition may be in the form of a sterile aqueous solution or dispersion. The pharmaceutical composition may also be formulated in a microemulsion, liposome, or other ordered structure suitable for high drug concentration.

The amount of the active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about 99% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for case of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, the pharmaceutical composition of the disclosure can be administered as a sustained release formulation, in which case less frequent administration is required.

For administration of the pharmaceutical composition of the disclosure, the dosage may range from about 0.0001 to 100 mg/kg body weight. An exemplary treatment regime entails administration once per week.

A "therapeutically effective dosage" of the pharmaceutical composition of the disclosure preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic antibody can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

The pharmaceutical compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the molecules of the disclosure can be formulated to ensure proper distribution in vivo. For example, to ensure that the therapeutic molecules of the disclosure cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al. (1988) *Biochem. Biophys. Res. Commun.* 153:1038; Bloeman et al., (1995) *FEBS Lett.* 357:140; M. Owais et al., (1995) *Antimicrob. Agents Chemother.* 39:180; Briscoe et al., (1995) *Am. J. Physiol.* 1233:134; Schreier et al., (1994) *J. Biol. Chem.* 269:9090; Keinanen and Laukkanen (1994) *FEBS Lett.* 346:123; and Killion and Fidler (1994) *Immunomethods* 4:273.

The pharmaceutical composition of the disclosure may have numerous in vitro and in vivo utilities involving, for example, treatment and/or prevention of e.g., cancers. The pharmaceutical composition of the disclosure may be administered to human subjects, to inhibit tumor growth.

Given the ability of the pharmaceutical composition of the disclosure to inhibit proliferation and survival of cancer cells, the disclosure provides a method for inhibiting growth of tumor cells in a subject comprising administering to the subject the pharmaceutical composition of the disclosure such that growth of the tumor is inhibited in the subject. Non-limiting examples of tumors that can be treated by the antibodies or molecules of the disclosure include, but not limited to, melanoma, lung cancer (e.g., non-small cell lung cancer), urothelial carcinoma, renal cell carcinoma, head and neck cancer, Hodgkin lymphoma, cancer with microsatellite instability or mismatch repair deficiency, gastric cancer, colorectal cancer, liver cancer (e.g., hepatocellular carcinoma), colon adenocarcinoma, and Merkel cell carcinoma, original and/or metastatic. Additionally, refractory or recurrent malignancies may be inhibited using the pharmaceutical composition of the disclosure.

In another aspect, the disclosure provides methods of combination therapy in which the pharmaceutical composition of the disclosure is co-administered with one or more additional antibodies or non-antibody agents that are effective in inhibiting tumor growth in a subject. In one embodiment, the disclosure provides a method for inhibiting tumor growth in a subject comprising administering to the subject the pharmaceutical composition of the disclosure with one or more additional antibodies, such as an anti-PD-1 antibody, and/or an anti-CTLA-4 antibody. The pharmaceutical composition of the disclosure may be used in combination with a chemotherapeutic agent, which is toxic to cells. Other therapies that may be combined with the pharmaceutical composition of the disclosure includes, but not limited to, interleukin-2 (IL-2) administration, radiation, surgery, or hormone deprivation. In certain embodiments, the subject is human.

The pharmaceutical composition of the disclosure may be used to treat infectious diseases, especially chronic infectious diseases, in a subject in need thereof. In certain embodiments, the diseases may be chronic viral infections, such as the chronic infections of hepatitis B virus (HBV), hepatitis C virus (HCV), human immunodeficiency virus (HIV), or simian immunodeficiency virus (SIV). In certain embodiments, the pharmaceutical composition of the disclosure may be administered with at least one anti-viral agent.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1

Construction of Cell Lines Stably Expressing PD-L1

Cell lines stably expressing human, monkey or mouse PD-L1 were constructed using HEK293A cells. Briefly, cDNA sequences encoding human, monkey or mouse PD-L1s (amino acid sequences set forth in SEQ ID NOs: 11, 12 and 13, respectively) were synthesized, and then subcloned into pLV-BGFP(2A)-Puro vectors (Beijing Inovogen, CN). Lentiviruses were generated in HEK293T cells (Cobioer, NJ, CN) by co-transfection of the resultant pLV-EGFP (2A)-Puro-PD-L1, psPAX and pMD2.G plasmids, according to the instruction in Lipofectamine® 3000 kit (Thermo Fisher Scientific, USA). Three days post co-transfection, the lentiviruses were harvested from the HEK293T cell culture supernatants (the culture medium containing DMEM (Cat #:SH30022.01, Gibco) with 10% FBS (Cat #:FND500, Excell)), and then used to infect HEK293A cells (Cobioer, NJ, CN) to generate HEK293A/human PD-L1 cells, HEK293A/monkey PD-L1 cells, and HEK293A/mouse PD-L1 cells. These HEK293A cells were cultured in DMEM (Cat #:SH30022.01, Gibco, USA) containing 10% FBS (Cat #:FND500, Excell, CN) and 0.2 ng/ml puromycin (Cat #:A11138-03, Gibco) for 7 days. The expressions of human and monkey PD-Lis were confirmed by FACS using commercially available anti-PD-L1 antibody (PB anti-human PD-L1 antibody, Cat #:393607, Biolegend, USA). Similarly, the expressions of mouse PD-L1 was measured by FACS using the PE-anti-mouse PD-L1 antibody (Cat #:124307, Biolegend, USA).

Example 2

Generation of Antibody Phage Library

Camelid anti-human PD-L1 sdAbs were generated by the phage display technique.

In particular, a *Camelus dromedarius* was injected with the recombinant human PD-L1 (ECD)-hFc protein (Cat #:10084-H02H, Sino Biological, CN) and the recombinant monkey PD-L1 (ECD)-hFc (Cat #:90251-C02H, Sino Biological, CN), according to the immunization scheme of Table 2. These two recombinant proteins were emulsified by sonication with an equal volume of Complete Freund's Adjuvant (Cat #:F5881-10*10 ML, SIGMA, US), or Incomplete Freund's Adjuvant (Cat #:FSS06-6*10 ML, SIGMA, US). One week post the last boost, 5 ml serum was collected from the camel, and tested for the antibody titers by ELISA using the recombinant human PD-L1 (ECD)-hFc protein (Cat #: 10084-H02H, Sino Biological, CN) and the recombinant monkey PD-L1 (ECD)-his (Cat #:10377-H08H, Sino Biological, CN).

Based on the ELISA data, 100 ml serum was collected from the camel, and extracted for total RNAs which were converted to cDNAs and used for amplifying $V_H$Hs using the nested PCR. Then, 20 μg pMECS phage display vectors and 10 μg $V_H$Hs were digested with PstI and NotI, and ligated. The resulting vectors were transformed into electrocompetent TG1 cells to construct the $V_H$H phage display library having about $1.2\times10^9$ cfu phages.

TABLE 2

| | Immunization scheme | | | | | |
|---|---|---|---|---|---|---|
| | Primary | 1st Boost | 2nd Boost | 3rd Boost | 4th Boost | Final boost |
| Day | 0 | 7 | 14 | 21 | 28 | 35 |
| Immunogen and | human PD-L1(ECD)- | human PD-L1(ECD) hFc | human PD-L1(ECD)- | human PD-L1(ECD)-hFc | human PD-L1(ECD)-hFc | human PD-L1(ECD)-hFc |

TABLE 2-continued

| | Immunization scheme | | | | | |
| | Primary | 1st Boost | 2nd Boost | 3rd Boost | 4th Boost | Final boost |
| --- | --- | --- | --- | --- | --- | --- |
| dose | hFc (200 µg) + monkey PD-L1(ECD)-hFc (200 µg) | (100 µg) + monkey PD-L1(ECD)-hFc (100 µg) | hFc (100 µg) + monkey PD-L1(BCD)-hFc (100 µg) | (100 µg) + monkey PD-L1(ECD)-hFc (100 µg) | (100 µg) + monkey PD-L1(BCD)-hFc (100 µg) | (100 µg) + monkey PD-L1(ECD)-hFc (100 µg) |
| Adjuvant | Complete Freund's | Incomplete Freund's | Incomplete Freund's | Incomplete Freund's | Incomplete Freund's | Incomplete Freund's |
| Administration route | Subcutaneous injections (s.c.) at neck | Subcutaneous injections (s.c.) at neck | Subcutaneous injection (s.c.) at neck | Subcutaneous injection (s.c.) at neck | Subcutaneous injection (s.c.) at neck | Subcutaneous injection (s.c.) at neck |

The TG1 cells in 200 µl culture medium were moved to and cultured in 2×TY culture medium overnight, during the cell culture, 40 µl VCSM13 helper phages were added. The phages were precipitated with PEG/NaCl, centrifuged and harvested. An ELISA plate was coated with 200 µg PD-L1 proteins in PBS with 100 nM NaHCO$_3$ (pH8.2) overnight at 4° ° C., added with 100 µl PBS with 3% BSA, incubated at room temperature for 2 h, added with 100 µl the phages as harvested above (2×10$^{11}$ tfu), and incubated at room temperature for 1 h. Then, the ELISA plate was washed with PBS with 0.05% Tween-20 for 5 times, to remove unbound phages. The phages specific to the PD-L1 proteins were digested with trypsin at the final concentration of 25 mg/ml, and used to infect the TG1 cells at the log phase. The TG1 cells were cultured at 37° C. for 1 h, and the phages were harvested for the next-round screening.

Three rounds of biopanning were carried out in total, after which 200 single bacterial colonies were cultured in the TB culture medium with 100 µg/ml ampicillin in 96-well deep well plates at 37° C. When the bacteria grew to the log phase, 1 mM IPTG was added to each well and the bacteria were cultured at 28° C. overnight. Crude antibodies were harvested by the osmotic swelling process, transferred to the antigen-coated ELISA plates, and incubated at room temperature for 1 h. The unbound antibodies were washed away by PBST, and the plates were added with 100 µl mouse anti-HA antibodies (1:2000 dilution, Covance) and incubated at room temperature for 1 h. The unbounded mouse-anti-HA antibodies were washed away by PBST, and the plates were added with 100 µl alkaline phosphatase (AP)-anti-mouse IgG antibodies (1:2000 dilution, Sigma), and incubated at room temperature for 1 h. The unbound AP-anti-mouse IgG antibodies were washed away with PBST, and the plates were added with the color development solution, incubated for 5-10 min, and read for the absorbance at 450 nm. A plate well was determined to be positive when its OD value was at least 5-fold higher than that of the control well. The bacteria showing positive binding results were cultured in LB culture medium with 100 µg/ml ampicillin with shaking, from which vectors were extracted and sequenced.

With the sequence analysis using Vector NTI®, 9 phages with distinct antibody sequences were obtained finally.

Example 3

Expression and Purification of Anti-PD-L1 sdAb-Fc Fusion Proteins

The 9 sdAbs as obtained in Example 2 were respectively fused to a heavy chain Fc region, wherein the C-terminus of each sdAb was linked to the N-terminus of the Fc region. Briefly, the sdAb sequences were obtained from the phages displaying the 9 sdAbs by PCR and sequenced, with the sequences and SEQ ID NOs summarized in Table 1 and Table 7. The DNA fragments each encoding a sdAb linked to a human IgG1 Fc region (SEQ ID NO: 10) were inserted into the pCDNA3.1 plasmids (Invitrogen, USA) between XhoI and BamHI.

HEK-293F cells (Cobioer, CN) were transfected with the expression vectors obtained above using PEI. Briefly, the HEK-293F cells were cultured in Free Style™ 293 expression medium (Cat #:12338-018, Gibco), and transfected with the expression vectors using polyethyleneinimine (PEI) at a DNA:PEI ratio of 1:3, 1.5 µg of DNAs per millimeter of cell medium. The transfected HEK-293F cells were cultured in an incubator at 37° C. under 5% CO$_2$ with shaking at 120 RPM. After 10-12 days, the cell culture supernatants were harvested, centrifuged at 3500 rpm for 5 min, and flowed through a 0.22 µm film filter to remove the cell debris. The fusion proteins as expressed were purified using pre-equilibrated Protein-A affinity columns (Cat #:17040501, GE, USA) and eluted with the elution buffer (20 mM citric acid, pH 3.0-3.5). The obtained fusion proteins were kept in PBS (pH 7.0) and measured for the concentrations using a NanoDrop® analyzer.

Example 4

Effect of Anti-PD-L1 sdAb-Fc Fusion Proteins on T Cell Activation

The anti-PD-L1 sdAb-Fc fusion proteins were tested for their capability to induce APC-mediated T cell activation in a mixed lymphocyte reaction (MLR) assay.

Briefly, PBMCs from a healthy human donor' blood sample were collected by density gradient centrifugation, suspended in RPMI1640 medium, and cultured in an incubator at 37° C. for 2 h. The adherent cells, i.e., the monocytes, were harvested, and cultured in RPMI1640 medium with 100 ng/ml recombinant human GM-CSF (Cat #:7954-GM, R&D, USA), 100 ng/ml recombinant human IL-4 (Cat #:6507-IL, R&D, USA) and 10% FBS. Three days later, half of the medium was replaced with the fresh one. On the 6$^{th}$ day of cell culture, the medium was replaced with that containing 100 ng/ml recombinant human GM-CSF. 100 ng/ml recombinant human IL-4, 10 ng/ml rhTNF-α (Cat #:210-TA-100, R&D, US), 1000 U/ml rhIL-6 (Cat #:7270-IL-025, R&D, US), 1 µg/ml PGE2 (Cat #:363-24-6, TOCRIS, US) and 10 ng/ml IL-1β (Cat #:210-LB-025, R&D, US), and the cells were cultured for another 2 days. PBMCs from another healthy human donor' blood sample were collected by density gradient centrifugation and suspended in RPMI1640 medium, and CD4$^+$ T cells were isolated from the PBMCs using Invitrogen Dynabeads® Untouched Human CD4$^+$ T cell isolation kit (Cat #:11346D, Thermal Fisher Scientific, USA) according to the manufacturer's instruction. The dendritic cells from the first donor and the CD4$^+$ T cells from the second donor were plated onto a 96-well U-shape plate at the cell density of 2.5×10$^4$ per well and 5×10$^4$ per well, respectively, with 150 µl culture medium in total. The plate was added with 50 µl anti-PD-L1 sdAb-Fc fusion proteins or an anti-HEL human IgG1 isotype control (Cat #:LT12031, LifeTein, USA) at the concentration of 0.1 to 10 µg/ml, and incubated for 72 h. The IFN-γ level was measured by ELISA using a kit (Cat #: SIF50, R&D, USA) following the manufacturer's instruction. The assay was done in triplicate.

As shown in FIG. 1, the highest IFN-γ levels were observed in the wells containing the fusion proteins with the anti-PD-L1 sdAb 10CA81 and 10CA192.

Example 5

Binding Capability of Anti-PD-L1 sdAb-Fc Fusion Proteins to PD-L1-Expressing HEK293A Cells The anti-PD-L1 sdAb-Fc fusion proteins of the disclosure were tested for their binding capability to human, monkey or mouse PD-L1 molecules on HEK293A cells, using the HEK293A/human PD-L1 cells, HEK293A/monkey PD-L1 cells and HEK293A/mouse PD-L1 cells generated in Example 1. Briefly, 10$^5$ HEK293A cells in 100 µl medium were plated onto a 96-well plate, which was added with 50 µl serially diluted anti-PD-L1 sdAb-Fc fusion proteins of the disclosure. After incubation at 4° C. for 1 h, the plate was washed with PBST for 3 times, added with PE-goat-anti-human IgG antibody (1:500 dilution, Cat #:PAI-86078, Thermofisher, USA), incubated at 4° C. for 1 h, washed with PBS for 3 times, and measured for fluorescence in a FACS analyzer (BD). The atezolizumab was prepared using the amino acid sequences disclosed in WO2013079174A1 (including the constant region sequences) and used as a positive control.

TABLE 3

| Binding capability of anti-PD-L1 sdAb-Fc fusion proteins to PD-L1-expressing cells | | | |
|---|---|---|---|
| | FACS (EC$_{50}$ M/L) | | |
| Fusion protein | HEK-293A/ human PD-L1 cells | HEK-293A/ monkey PD-L1 cells | HEK-293A/ mouse PD-L1 cells |
| 10CA81-Fc | 2.3E−10 | 1.3E−10 | No binding |
| 10CA192-Fc | 5.1E−10 | 1.7E−10 | No binding |
| atezolizumab | 3.7E−10 | 1.3E−10 | No binding |

The data showed that all the anti-PD-L1 sdAb-Fc fusion proteins of the disclosure bound with high capability to cell surface human and monkey PD-L1 proteins, but did not bind mouse PD-L1 molecules. The EC$_{50}$ values of two representative fusion proteins containing 10CA81 and 10CA192 respectively were summarized in Table 3. Further, as shown in FIG. 2, the two fusion proteins, 10CA81-Fc and 10CA192-Fc, bound to the HEK293A/human PD-L1 cells (A) and HEK293A/monkey PD-L1 cells (B) with relatively high activity in a concentration dependent manner.

Example 6

Effect of Anti-PD-L1 sdAb-Fc Fusion Proteins on PD-1-PD-L1 Interaction

The anti-PD-L1 sdAb-Fc fusion proteins were tested for their blocking activity on PD-1-PD-L1 interaction using the HEK293A/human PD-L1 cells as generated in example 1. Briefly, 10$^5$ HEK293A/human PD-L1 cells in 100 µl medium were plated onto a 96-well plate, which was added with 50 µl serially diluted anti-PD-L1 sdAb-Fc fusion proteins of the disclosure. After incubation at 4° C. for 1 h, the plate was washed with PBST for 3 times, added with 100 µl 200 µg/ml recombinant PD1-mFc proteins (Cat #:10377-H05H, Sino biological, CN), incubated at 4° C. for 1 h, washed with PBST for 3 times, and added with PE-goat-anti-mouse IgG antibody (1:500 dilution, Cat #:405307, BioLegend, USA). After incubation at 4° C. for 1 h, the plate was washed with PBST for 3 times, and measured for fluorescence in a FACS analyzer (BD).

TABLE 4

| Blocking activity on PD-1-PD-L1 interaction | |
|---|---|
| Fusion protein | EC$_{50}$ (M/L) |
| atezolizumab | 1.8E−10 |
| 10CA81-Fc | 1.1E−10 |
| 10CA192-Fc | 1.8E−10 |

According to the data, only 2 fusion proteins, out of 9, were not able to block PD-1-PD-L1 interaction, and the EC$_{50}$ values of two representative fusion proteins containing 10CA81 and 10CA192 were summarized in Table 4. As shown in FIG. 3, the two fusion proteins, 10CA81-Fc and 10CA192-Fc, blocked the interaction of PD-L1 with PD-1 in a concentration dependent manner, with the blocking activity comparable to or better than that of atezolizumab.

Example 7

Effect of Anti-PD-L1 sdAb-Fc Fusion Proteins on T Cell Activation

Following the protocol in Example 4, two exemplary fusion proteins, i.e., 10CA81-Fc and 10CA192-Fe, were tested for their capability to induce APC-mediated T cell activation in a mixed lymphocyte reaction (MLR) assay, in comparison with atezolizumab.

As shown in FIG. 4, the two fusion proteins increased IFN-γ secretion by T cells, as compared to the negative control, in a concentration dependent manner. Further, the two exemplary fusion proteins of the disclosure shower higher capability than atezolizumab at certain concentrations.

Example 8

Humanization of Anti-PD-L1 sdAbs

Based on the assays above, two camelid sdAbs, i.e., 10CA81 and 10CA192, were humanized and further investigated. Humanization of the antibodies was conducted using the well-established CDR-grafting method (U.S. Pat. No. 5,225,539) as described in detail below.

To select the acceptor frameworks for humanization of the two sdAbs, the two V$_H$H sequences were blasted against the human immunoglobulin gene database in NCBI website (http://www.ncbi.nlm.nih.gov/igblast/). The human germline IGVH with the highest homology to the two sdAbs were selected as the acceptors for humanization. For both sdAbs, the human heavy chain acceptor IGHV1-46*01 was selected. The three dimensional structures were simulated for the variable domains of the two sdAbs, in order to identify key framework residues that might be playing important roles in supporting CDR loop structures, thus designing back mutations in the humanized antibodies.

TABLE 5

Amino acid residue for back-mutations

| mAb ID | Residue mutations |
|---|---|
| 10CA81-V$_H$H1 | none |
| 10CA81-V$_H$H2 | E1Q, T28A |
| 10CA81-V$_H$H3 | W108K, I70T |
| 10CA81-V$_H$H4 | E1Q, T28A, W108K, I70T |
| 10CA81-V$_H$H5 | E1Q, T28A, F29V, A97S, K98Q, W108K |
| 10CA192-V$_H$H1 | none |
| 10CA192-V$_H$H2 | E1Q, T28A |
| 10CA192-V$_H$H3 | W108K, I70T |
| 10CA192-V$_H$H4 | E1Q, T28A, W108K, I70T |
| 10CA192-V$_H$H5 | E1Q, T28A, I70T, A97S, K98Q, W108K |

Seven (7) residues were identified for back mutations for the sdAb 10CA81, namely E1Q, T28A, F29V, I70T, A97S, K98Q, and W108K, and 6 residues for the sdAb 10CA192, namely E1Q, T28A, A97S, K98Q, W108K and I70T.

As shown in Table 5, 5 humanized V$_H$Hs were designed for 10CA81, with a total of 5 humanized antibodies were obtained; while 5 humanized VHHs were designed for 10CA192, with a total of 5 humanized antibodies were obtained. The sequences and SEQ ID NOs can be found in Table 1, Table 5 and Table 7.

The nucleotide sequences each encoding a humanized V$_H$H and a human IgG constant region (SEQ ID NO: 10) were chemically synthesized and then subcloned into GS expression vectors (Invitrogen, USA) using the EcoR I/Xho I or Cla I/Hind III restriction sites. All expression constructs were checked by DNA sequencing. Ten (10) anti-PD-L1 humanized sdAb-Fc fusion proteins were expressed using the EXPiCHO® expression systems (Invitrogen, USA), and purified following the protocol described in Example 3.

Example 9

Binding Capability/Affinity Determination of Anti-PD-L1 Humanized sdAb-Fc Fusion Proteins The anti-PD-L1 humanized sdAb-Fc fusion proteins were tested for their binding capability to the HEK293A/human PD-L1 cells, HEK293A/monkey PD-L1 cells and HEK293A/mouse PD-L1 cells generated in Example 1, respectively, following the protocol of Example 5. The results were shown in FIG. 5 and FIG. 6.

These fusion proteins were also measured for their binding affinity to human and monkey PD-L1 proteins by BIAcore™ 8K (GE Life Sciences, USA), Briefly. 100-200 response units (RUs) of human PD-L1 (ECD)-his protein (Cat #:10084-H08H, Sino Biological, CN) or monkey PD-L1 (BCD)-his protein (Cat #: 90251-C08H, Sino Biological, CN) were coupled to CMS biosensor chips (Cat #:BR-1005-30, GB Life Sciences, US). The un-reacted groups in the chips were blocked with 1 M ethanolamine. Then, serially diluted fusion proteins of the disclosure at concentrations ranging from 0.3 µM to 10 µM were injected into the SPR running buffer (HBS-EP buffer, pH17.4, Cat #:BR-1006-69, GE Life Sciences, US) at 30 µL/min. The binding affinity was calculated with the RUs of blank controls subtracted, and the association rate ($k_a$) and dissociation rate ($k_d$) were determined using the one-to-one Langmuir binding model (BIA Evaluation Software, GE Life Sciences, US). The equilibrium dissociation constant $K_D$ was calculated as the $k_d/k_a$ ratio. The binding affinity of the fusion proteins to the human PD-L1 protein were summarized in Table 6.

According to FIG. 5 and FIG. 6, the anti-PD-L1 humanized sdAb-Fc fusion proteins of the disclosure showed high binding capabilities to human and monkey PD-L1 proteins, which were comparable to those of the corresponding anti-PD-L1 camelid sdAb-Fc fusion proteins.

As shown in Table 6, the anti-PD-L1 humanized sdAb-Fc fusion proteins had comparable binding affinity to the human PD-L1 protein to atezolizumab.

TABLE 6

Binding affinity of anti-PD-L1 humanized
sdAb-Fc fusion proteins to human PD-L1

| Fusion protein | Human PD-L1 | | |
|---|---|---|---|
| | $K_a$ | $K_d$ | $K_D$ |
| 10CA81-V$_H$H5-Fc | 3.07E+06 | 1.39E−02 | 4.54E−09 |
| 10CA81-V$_H$H4-Fc | 1.89E+06 | 4.27E−03 | 2.26E−09 |
| 10CA192-V$_H$H2-Fc | 5.07E+06 | 4.05E−03 | 8.00E−10 |
| 10CA192-V$_H$H4-Fc | 4.07E+06 | 2.76E−03 | 6.79E−10 |
| atezolizumab | 1.49E+06 | 2.58E−04 | 1.73E−10 |

Example 10

Effect of Anti-PD-L1 Humanized sdAb-Fc Fusion Proteins on PD-L1-PD-1 Interaction Following the protocol of Example 6, the anti-PD-L1 humanized sdAb-Fc fusion proteins were tested for their ability to block the PD-1-PD-L1 interaction using the HEK293A/human PD-L1 cells generated in Example 1. Briefly, 105 HEK293/human PD-L1 cells in 100 µl medium were plated onto a 96-well plate, which was added with 50 µl serially diluted anti-PD-L1 humanized sdAb-Fc fusion proteins of the disclosure. After incubation at 4° C. for 1 h, the plate was washed with PBST for 3 times, added with 100 µl 200 µg/ml recombinant PD1-mFc proteins (Cat #: 10377-H05H, Sino biological, CN), incubated at 4° C. for 1 h, washed with PBST for 3 times, and added with PE-goat-anti-mouse IgG antibody (1:500 dilution, Cat #:405307, BioLegend, USA). After incubation at 4° C. for 1 h, the plate was washed with PBST for 3 times, and measured for fluorescence in a FACS analyzer (BD).

As shown in FIG. 7, all the anti-PD-L1 humanized sdAb-Fc fusion proteins of the disclosure significantly blocked PD-1-PD-L1 binding/interaction with comparable capability to their corresponding anti-PD-L1 camelid sdAb-Fc fusion proteins.

Example 11

Effect of Anti-PD-L1 Humanized sdAb-Fc Fusion Proteins on T Cell Activation

Following the protocol of Example 4, the anti-PD-L1 humanized sdAb-Fc fusion proteins were tested for their ability to activate T cells. The IFN-γ levels were measured using a commercially available kit (Cat #: STA00C, R&D, USA) according to the manufacturer's instruction.

The results were shown in FIG. 8. All the anti-PD-L1 humanized sdAb-Fc fusion proteins of the disclosure as tested promoted T cell activity, resulting in e.g., increased IFN-γ levels, in a concentration dependent manner. The fusion proteins containing 10CA81-V$_H$H5, 10CA81-V$_H$H4, 10CA192-V$_H$H2 and 10CA 192-V$_H$H4 showed the highest activity in T cell activation.

Example 12

In Vivo Anti-Tumor Activity of Anti-PD-L1 Humanized sdAb-Fc Fusion Proteins

The in vivo anti-tumor activity of the anti-PD-L1 humanized sdAb-Fc fusion proteins was tested, using the huPD-L1 transgenic mice (GemPharmatech Co. Ltd., CN) implanted with MC38 cells (murine colon adenocarcinoma cells).

Briefly, on Day 0, the mice were subcutaneously injected with $1 \times 10^6$ MC38 cells at the left or right flank, and randomly allocated into 6 groups, 10 mice per group. The mice in Group 1 to Group 6 were intraperitoneally administered with PBS (20 mg/kg, G1), 10CA81-V$_H$5-Fc fusion protein (20 mg/kg, G2), 10CA81-V$_H$H4-Fc fusion protein (20 mg/kg, G3), 10CA192-V$_H$H2-Fc fusion protein (20 mg/kg, G4), 10CA192-V$_H$H4-Fc fusion protein (20 mg/kg, G5), and atezolizumab (20 mg/kg, G6), respectively, on Day 0, 4, 7, 11, 14 and 18.

Tumor sizes and mouse body weights were monitored over time. In specific, the tumor size was determined by measuring by a caliper the length (the longest diameter) and the width (the diameter perpendicular to the length) of a tumor and calculating the volume as $0.5 \times D \times d^2$. The test was terminated before the tumor sizes in the administration group reached 3.5 cm$^3$. One-way ANOVA was used to identify tumor size differences among groups.

The results were shown in FIG. 9. It can be seen that all the anti-PD-L1 humanized sdAb-Fc fusion proteins significantly inhibited tumor growth, with the 10CA192-V$_H$H4-Fc fusion protein having higher in vivo anti-tumor efficacy than atezolizumab.

The sequences in the present application are summarized in Table 7 below.

TABLE 7

Sequences
Description/Sequences/SEQ ID NO.

V$_H$H-CDR1 of camelid and humanized 10CA81 and 10CA193
DYAMT (SEQ ID NO: 1)

V$_H$H-CDR2 of camelid and humanized 10CA81 and 10CA193
TINSGGQSSSYX1BSX2KG (SEQ ID NO: 2)

V$_H$H-CDR3 of camelid and humanized 10CA81 and 10CA193
GVYMPWKXP (SEQ ID NO: 3)

V$_H$H-CDR2 of camelid and humanized 10CA81
TINSGGQSSSYTNSAKG (SEQ ID NO: 2, X1 = T, B = N, X2 = A)

V$_H$H-CDR3 of camelid and humanized 10CA81
GVYMPWKKP (SEQ ID NO: 3, X = K)

V$_H$H-CDR2 of camelid and humanized 10CA192
TINSGGQSSSYLDSVKG (SEQ ID NO: 2, X1 = L, B = D, X2 = V)

V$_H$H-CDR3 of camelid and humanized 10CA192
GVYMPWKAP (SEQ ID NO: 3, X = A)

V$_H$H of camelid 10CA81
QVQLQESGGGLVQPGGSLRLSCVASGFAFSDYAMTWVRQAPGKGLEWVSTINSG
GQSSSYTNSAKGRETTSRDNAKNTLYLQLNSLKIEDTAMYYCSQGVYMPWKKPK
GQGTQVTVSS (SEQ ID NO: 4)

V$_H$H of 10CA81-V$_H$H4
QVQLLESGQGLVQPGGSLRLSCAASGFAFSDYAMTWVRQAPGKGLEWVSTINSG
GQSSSYINSAKGRFTTSRDNSKNTLYLQMNSLRAEDTAVYYCAKGVYMPWKKP
KGQGTLVTVSS (SEQ ID NO: 5)

V$_H$H of 10CA81-V$_H$H5
QVQLLESGGGLVQPGGSLRLSCAASGFAVSDYAMTWVRQAPGKGLEWVSTINSG
GQSSSYTNSAKGRFTISRDNSKNTLYLQMNSLRAEDTAVYYCSQGVYMPWVKKPK
GQGTLVTVSS (SEQ ID NO: 6)

V$_H$H of camelid 10CA192
QVQLQESQGGSVQAGQSLMLSCAASQFAFSDYAMTWVRQAPGKGLEWVSTINS
GGQSSSYLDSVKGRFTSTRDNAKNMLYLQLNSLKIEDTAMYYCSQGVYMPWKA
PKGQGTQVTVSS (SEQ ID NO: 7)

V$_H$H of 10CA192-V$_H$H2
QVQLLESGGGLVQPGGSLRLSCAASGFAFSDYAMTWVRQAPGKGLBWVSTINSG
GQSSSYLDSVKGRFTISRDNSKNTLYLQMNSLRAEDTAVYYCAKGVYMPWKAP
WGQGTLVTVSS (SEQ ID NO: 8)

TABLE 7-continued

Sequences
Description/Sequences/SEQ ID NO.

V_HH of 10CA192-V_HH4
QVQLLESGQGLVQPGGSLRLSCAASGFAFSDYAMTWVRQAPQKGLEWVSTINSG
GQSSSYLDSVKGRFTSSRDNSKNTLYLQMNSLRAEDTAVYYCAKGVYMPWKAP
KQQGTLVTVSS (SEQ ID NO: 9)

Human IgG1 constant region (CH2-CH3)
EPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVESCSVMHEALHN
HYTQKSLSLSPGK (SEQ ID NO: 10)

Human PD-L1
MRIFAVFIFMTYWHLLNAFTVTVPKDLYVVEYQSNMTIECKFPVEKQLDLAALIV
YWEMEDKNIIQFVHGEEDLKVQHSSYRQRARLLKDQLSLGNAALQITDVKLQDA
GVYRCMISYGGADYKRITVKVNAPYNKINQRILVVDPVTSEHELTCQAEGYPKAB
VIWTSSDHQVLSGKTTTTNSKREEKLFNVTSTLRINTTTNEIFYCTFRRLDPEENHT
AELVIPELPLAHPPNERTHLVILGAILLCLGVALTFIFRLRKGRMMDVKKCGIQDT
NSKKQSDTHLEET (SEQ ID NO: 11)

Monkey PD-L1
MRIFAVFIFTYWHLLNAFTVTVPKDLYVVEYGSNMTIECKFPVEKQLDLISLIVY
WEMEDKNIIQFVHGBEDLKVQHSNYRQRAQLLKDQLSLGNAALRITDVKLQDAG
VYRCMISYGGADYKRITVKYNAPYNKINQRILVVDPVTSEHELTCQAEGYPKAEV
IWTSSDHQVLSGKTTTTNSKREEKLLNVTSTLRINTTANEIFYCIFRRLDPEENHTA
ELVIPELPLALPPNERTHLVILGAIFLLLGVALTFIFYLRKGRMMDMKKCGIRVINS
KKQRDTQLEET (SEQ ID NO: 12)

Mouse PD-L1
MRIFAGIIFTACCHLLRAFTITAPKDLYVVEYGSNVTMECRFPVERELDLLALVVY
WEKEDEQVIQFVAGEEDLKPQHSNFRGRASLPKDQLLKGNAALQITDVKLQDAG
VYCCIISYGGADYKRITIKVNAPYRKINQRISVDPATSEHELICQAEGYPEABVIWT
NSDHQPVSGKRSVTTSRTEGMLLNVTSSLRVNATANDVFYCTFWRSQPGQNHTA
BLIIPELPATHPPQNRTHWVLLGSILLFLIVVSTVLLFLRKQVRMLDVEKCGVEDTS
SKNRNDTQFEET (SEQ ID NO: 13)

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. An isolated molecule, which binds PD-L1, comprising a heavy chain variable region, wherein the heavy chain variable region comprises a CDR1, a CDR2 and a CDR3 respectively comprising the amino acid sequences of (1) SEQ ID NOs: 1, 2 (X1=T, B=N, X2=A) and 3 (X=K); or (2) SEQ ID NOs: 1, 2 (X1=L, B=D, X2=V) and 3 (X=A).

2. The molecule according to claim 1, wherein the heavy chain variable region comprises an amino acid sequence having at least 85%, 86%, 87%, 88%, 89%, 90%, 91%, 92%, 93%, 94%, 95%, 96%, 97%, 98%, 99% or 100% sequence identity to SEQ ID NOs: 4, 5, 6, 7, 8 or 9.

3. The molecule according to claim 1, further comprising an immunoglobulin heavy chain constant region, wherein the heavy chain variable region and the immunoglobulin heavy chain constant region form a recombinant fusion protein.

4. The molecule according to claim 3, wherein the immunoglobulin heavy chain constant region is an IgG1 constant region or its Fc region.

5. The molecule according to claim 4, wherein the immunoglobulin heavy chain constant region comprises the amino acid sequence of SEQ ID NO: 10.

6. The molecule according to claim 5, which is a dimer of the recombinant fusion protein.

7. The molecule according to claim 1, which (a) binds human PD-L1, (b) binds monkey PD-L1, (c) does not bind mouse PD-L1, (d) blocks PD-1-PD-L1 binding, (e) activates immune cells, and (f) has in vivo anti-tumor activity.

8. An isolated molecule, which binds PD-L1, comprising a heavy chain variable region, wherein the heavy chain variable region comprises a CDR1, a CDR2 and a CDR3 from a heavy chain variable region comprising the amino acid sequences of SEQ ID NOs: 4, 5, 6, 7, 8 or 9.

9. A nucleic acid molecule encoding the molecule according to claim 1.

10. An expression vector, comprising the nucleic acid molecule according to claim 9.

11. A host cell, comprising the expression vector according to claim 10.

12. A pharmaceutical composition comprising the molecule according to claim 1, and a pharmaceutically acceptable carrier.

13. A method for treating a PD-L1 associated disease in a subject in need thereof, comprising administering to the subject the pharmaceutical composition according to claim 12.

14. The method according to claim 13, wherein the disease is tumor.

15. The method according to claim 14, wherein the tumor is a solid or hematologic tumor.

16. The method according to claim 14, wherein the tumor is melanoma, lung cancer, urothelial carcinoma, renal cell carcinoma, head and neck cancer, Hodgkin lymphoma, cancer with microsatellite instability or mismatch repair deficiency, gastric cancer, colorectal cancer, liver cancer, colon adenocarcinoma, or Merkel cell carcinoma.

17. A method for enhancing an immune response in a subject in need thereof, comprising administering to the subject the pharmaceutical composition according to claim 12.

* * * * *